(12) United States Patent
Chen et al.

(10) Patent No.: US 7,423,053 B2
(45) Date of Patent: Sep. 9, 2008

(54) 4-AMINOTHIAZOLE DERIVATIVES

(75) Inventors: Li Chen, Shanghai (CN); Xin-Jie Chu, Livingston, NJ (US); Allen John Lovey, North Caldwell, NJ (US); Chunlin Zhao, Livingston, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 534 days.

(21) Appl. No.: 11/170,636

(22) Filed: Jun. 29, 2005

(65) Prior Publication Data

US 2006/0014958 A1 Jan. 19, 2006

Related U.S. Application Data

(60) Provisional application No. 60/588,184, filed on Jul. 15, 2004.

(51) Int. Cl.
*A61K 31/4523* (2006.01)
*C07D 417/02* (2006.01)

(52) U.S. Cl. ........................... 514/326; 546/209
(58) Field of Classification Search ............ 546/209
See application file for complete search history.

(56) References Cited

U.S. PATENT DOCUMENTS

| 6,262,096 B1 | 7/2001 | Kim et al. |
| 6,569,878 B1 | 5/2003 | Chong et al. |
| 7,211,576 B2 * | 5/2007 | Ding et al. ............ 514/231.5 |
| 2003/0220326 A1 | 11/2003 | Chong et al. |

FOREIGN PATENT DOCUMENTS

| WO | WO 99/21845 | 5/1999 |
| WO | WO 01/19825 | 3/2001 |
| WO | WO 01/38315 | 5/2001 |
| WO | WO 01/56567 A1 | 8/2001 |
| WO | WO 01/79198 | 10/2001 |
| WO | WO 03/011843 | 2/2003 |

OTHER PUBLICATIONS

De Azevedo et al., Eur. J. Biochem., 243, pp. 518-526 (1997).
Sielecki et al., J. Med. Chem., 43, pp. 1-18 (2000).
Harrington et al., Proc. Natl. Acad. Sci. USA, 95, pp. 11945-11950 (1998).
Garrett et al., Current Opin. Genetics Develop., 9, pp. 104-111 (1999).
Hoessel et al., Nature Cell Biology, 1, pp. 60-67 (1999).
Sielecki et al., Bioorg. Med. Chem. Lett., 11, pp. 1157-1160 (2001).
Nugiel et al., J. Med. Chem., 44, pp. 1334-1336 (2001).
Fry et al., J. Biol. Chem., 276, pp. 16617-16623 (2001).
Soni et al., Biochem. Biophys. Res. Commun., 275, pp. 877-884 (2000).
Jeong et al., Bioorg. Med. Chem. Lett., 10, pp. 1819-1822 (2000).
Ryu et al., Bioorg. Med. Chem. Lett., 10, pp. 461-464 (2000).
Reinhold et al., J. Biol. Chem., 273, pp. 3803-3807 1998).
Toogood et al., J. Med. Chem., 43, pp. 4606-4616 (2000).
Wilkinson et al., Emerging Drugs, 5, pp. 287-297 (2000).
Dumas, J., Exp. Opin. Ther. Patents, 11, pp. 405-429 (2001).
Fischer, P. M., Curr. Opin. in Drug Discov. and Develop., 4, pp. 623-634 (2001).
Meijer et al., Eur. J. Biochem., 267, pp. 5983-5994 (2000).
Honma et al., 221st National ACS Meeting., Medi. 136 (2001).
Carlson et al., Cancer Res., 56, pp. 2973-2978 (1996).
Kakeya et al., Cancer Res., 58, pp. 704-710 (1998).
Mgbonyebi et al., Cancer Res., 59, pp. 1903-1910 (1999).
Zaharevitz et al., Cancer Res., 59, pp. 2566-2569 (1999).
Harper, J. W., Cancer Surveys, 29, pp. 91-107 (1997).

* cited by examiner

*Primary Examiner*—Kamal A Saeed
(74) *Attorney, Agent, or Firm*—George W. Johnston; Patricia S. Rocha-Tramaloni; Gene J. Yao

(57) ABSTRACT

Novel 4-aminothiazole derivatives are disclosed. These compounds inhibit cyclin-dependent kinases. These compounds and their pharmaceutically acceptable salts and esters have antiproliferative activity and are useful in the treatment or control of cancer, in particular solid tumors. This invention is also directed to pharmaceutical compositions containing such compounds and to methods of treating or controlling cancer, most particularly the treatment or control of breast, lung, colon and prostate tumors. Also disclosed are intermediates useful in the preparation of these novel 4-aminothiazole derivatives.

11 Claims, No Drawings

4-AMINOTHIAZOLE DERIVATIVES

PRIORITY TO RELATED APPLICATIONS

This application claims the benefit of Provisional Application(s) Ser. No. 60/588,184, filed Jul. 15, 2004.

FIELD OF THE INVENTION

The present invention relates to novel 4-aminothiazole derivatives that inhibit cyclin-dependent kinases. These compounds and their pharmaceutically acceptable salts and esters have antiproliferative activity and are useful, inter alia, in the treatment or control of cancer, in particular solid tumors. This invention also relates to pharmaceutical compositions containing such compounds and to methods of treating or controlling cancer, most particularly the treatment or control of breast, lung, colon and prostate tumors. Finally, this invention is also directed to novel intermediate compounds useful in the preparation of the novel 4-aminothiazole derivatives herein disclosed.

BACKGROUND OF THE INVENTION

Uncontrolled cell proliferation is the hallmark of cancer. Cancerous tumor cells typically have some form of damage to the genes that directly or indirectly regulate the cell-division cycle.

The progression of cells through the various phases of the cell cycle is regulated by a series of multienzyme complexes consisting of a regulatory protein, a cyclin, and a kinase. These kinases are called cyclin-dependent kinases (Cdks). The Cdks are expressed throughout the cell cycle, while the levels of the cyclins vary depending on the stage of the cell cycle.

The four primary phases of cell cycle control are generally describes as $G_1$, S, $G_2$, and M. Some essential enzymes for cell cycle control appear to be cyclin D/Cdk4, cyclin D/Cdk6, cyclin E/Cdk2, cyclin A/Cdk2, and cyclin B/Cdk1 (also known as Cdc2/cyclin B). Cyclin D/Cdk4, cyclin D/Cdk6, and cyclin E/Cdk2 control passage through the $G_1$-phase and the $G_1$- to S-phase transition by phosphorylation of the retinoblastoma phosphoprotein, pRb. Cyclin A/Cdk2 regulates passage through the S-phase, and cyclin B/Cdk1 controls the $G_2$ checkpoint and regulates entry into M (mitosis) phase.

The cell cycle progression is regulated by Cdk1 (cdc2) and Cdk2 beyond early $G_1$ when cells are committed to cytokinesis. Therefore, drug inhibition of these Cdks is likely not only to arrest cell proliferation, but also to trigger apoptotic cell death. Once the cells pass the $G_1$ restriction point and are committed to S phase, they become independent of growth factor stimulation for continued cell cycle progression.

Following completion of DNA replication, cells enter the $G_2$ phase of the cell cycle in preparation for M phase and cytokinesis. Cdk1 has been shown to regulate passage of cells through these later phases of the cell cycle in association with both cyclins A and B. Complete activation of Cdk1 requires both cyclin binding and specific phosphorylation (Morgan, D. O., De Bondt, H. L., *Curr. Opin. Cell. Biol.* 1994, 6, 239-246). Once activated, Cdk1/cyclin complexes prepare the cell for division during M phase.

The transition from $G_1$ phase into S phase as stated above is regulated by the complex of Cdk4 with cyclin D and Cdk2. with cyclin E. These complexes phosphorylate the tumor suppressor protein Retinoblastoma (pRb), releasing the transcription factor E2F and allowing the expression of genes required in S phase (Nevins, J. R. *Science* 1992, 258, 424-429; Lavia, P. *BioEssays* 1999, 21, 221-230). Blocking the activity of the Cdk4/cyclin D and Cdk2/cyclin E complexes arrests the cell cycle in $G_1$ phase. For example, the proteins of the INK4 family, including p16$^{INK4a}$, which block the kinase activity of the Cdk4/cyclin D complex, cause arrest in $G_1$ (Sherr, C. J. *Science* 1996, 274, 1672-1677). The specific block has been reviewed (Vidal, A. *Gene* 2000, 247, 1-15).

Recent experiments show that the complex of Cdk4 with cyclin D3 also plays a role in cell cycle progression through $G_2$ phase. Inhibition of this complex, either by p16 or using a dominant negative Cdk4, results in arrest in $G_2$ phase in cells that do not express pRb (Gabrielli B. G. et al. *J. Biol. Chem.* 1999, 274, 13961-13969).

Numerous defects in the pRb pathway have been shown to be involved in various cancers. For example, overexpression of Cdk4 has been observed in cases of hereditary melanoma (Webster, K. R. *Exp. Opin. Invest Drugs* 1998, 7, 865-887); cyclin D is overexpressed in many human cancers (Sherr, C. J. *Science* 1996, 274, 1672-1677); p16 is mutated or deleted in many tumors (Webster, K. R. *Exp. Opin. Invest. Drugs* 1998, 7, 865-887); and pRb function is lost through mutation or deletion in many human cancers (Weinberg, R. A. *Cell* 1995, 81, 323-330). Defects in this pathway have also been shown to have an effect on prognosis. For example, loss of p16 is correlated with poor prognosis in non-small-cell lung carcinoma (NSCLC) and malignant melanoma (Tsihlias, J. et al. *Annu. Rev. Med.* 1999, 50, 401-423). Abnormalities of cyclin D1 and/or pRb at the gene and/or expression level were present in more than 90% of a series of non-small cell lung cancer specimens, indicating that cyclin D1 and/or pRb represent an important step in lung tumorigenesis (Marchetti, A. et al. *Int J. Cancer* 1998, 75, 573-582). In 49 out of 50 pancreatic carcinomas (98%), the pRb/p16 pathway was abrogated exclusively through inactivation of the p16 gene and cyclin D connected (Schutte, M. et al. *Cancer Res.* 1998, 57, 3126-3134). For a review on the relation between expression of pRb and the cyclin/cyclin dependent kinases in a number of tissues see Teicher, B. A. *Cancer Chemother. Pharmacol.* 2000, 46, 293-304.

Because of the involvement of the Cdk4/cyclin D/pRb pathway in human cancer through its role in regulating progression of the cell cycle from $G_1$ to S phase, and the potential therapeutic benefit from modulating this pathway, there has been considerable interest in agents that inhibit or promote elements of this pathway. For example, effects on cancer cells have been shown using antibodies, antisense oligonucleotides and overexpression or addition of proteins involved in the pathway. See, e.g., Lukas, J. et al. *Nature* 1995, 79, 573-582; Nevins, J. R. *Science* 1992, 258, 424-429; Lim, I. K. et al. *Molecular Carcinogenesis* 1998, 23, 25-35; Tam, S. W. et al. *Oncogene* 1994, 9, 2663-2674; Driscoll, B. et al. *Am. J. PhysioL* 1997, 273 (*Lung Cell. Mol. Physiol.*), L941-L949; and Sang, J. et al. *Chin. Sci. Bull.* 1999, 44, 541-544).

The role of cdks in the regulation of cellular proliferation is thus well established. For example, as shown above, there is an extensive body of literature validating the use of compounds inhibiting targets in the Cdk4, Cdk2 and Cdk1 pathways as anti-proliferative therapeutic agents. Inhibitors of cellular proliferation thus act as reversible cytostatic agents that are useful in the treatment of disease processes which feature abnormal cellular growth, such as cancers and other cell proliferative disorders including, for example inflammation (e.g. benign prostate hyperplasia, familial adenomauosis, polyposis, neuro-fibromatosis, atherosclerosis, pulmonary fibrosis, arthritis, psoriasis, inflammatory bowel disease, transplantation rejections infections), viral infections (including, but not limited to herpervirus, poxvirus, Epstein- Barr virus), autoimmune disease (e.g. lupus, rheumatoid arthritis, psoriasis, inflammatory bowel disease), neurodegenerative disorders (including but not limited to Alzheimer's disease), and neurodegenerative diseases (e.g. Parkinson's disease, amyotrophic lateral sclerosis, retinitis pigmentosa, spinal muscular atrophy, and cerebral degeneration).

Several distinct classes of small molecules have been identified as inhibitors of Cdks: olomoucine and other purine analogs, flavopiridol, staurosporine, UCN-01 and other indolocarbazoles, 9-hydroxyellipticine, indirubin, paullones, diaryl ureas, quinazolines, indopyrazoles, [2,3-d] pyridopyrimidines, fascaplysin, aminothiazoles, diaminothiazoles, p-teridinones, and pyrazoles or example (Carlson et. al., *Cancer Res.* 1996, 56, 2973-2978: De Azevedo et al., *Eur. J. Biochem.*, 1997, 243, 518-526; Bridges, A. J., *Exp. Opin. Ther. Patents.* 1995, 5,12451257; Reinhold et al., *J. Biol. Chem.* 1998, 278, 3803-3807; Kakeya, H. et. al., *CancerRes.* 1998, 58, 704-710; Harper, J. W., *Cancer Surveys* 1997, 29, 91-107; Harrington, E. A., et al., *Proc. Natl. Acad. Sci. USA* 1998, 95, 11945-11950; Meijer, L., et al., *Eur. J. Biochem.* 2000, 267, 5983-5994; Garrett, M. D. et. al., *Current Opin. Genetics Develop.* 1999, 9, 104-111; Mgbonyebi, O. P. et al., *Cancer Res.* 1999, 59, 1903-1910; Hoessel et al., *Nature Cell Biology.* 1999, 1, 60-67; Zaherevitz et al., *Cancer Res.*, 1999, 59, 2566-2569; Honma, T., et al., 221st *National ACS Meeting.* 2001: Medi 136; Sielecki, T. M., et al., *Bioorg. Med. Chem. Lett.* 2001, 11, 1157-1160; Nugiel, D. A., et al., *J. Med. Chem.*, 2001, 44, 1334-1336; Fry, D. W. et al., *J. Biol. Chem.* 2001, 276, 16617-15523; Soni, R., et al., *Biochem. Biophys. Res. Commun.* 2000, 275, 877; Ryu, C-K. et al., *Bioorg. Med. Chem. Lett.*, 2000, 10, 461; Jeong, H-W., et al., *Bioorg. Med. Chem. Lett.* 2000, 10, 1819; Toogood et al., *J. Med. Chem.*, 2000, 43, 4606-4616; Chong, W., Fischer, *Curr. Opin. in Drug Discov. and Develop.*, 2001, 4, 623-634, WO0009921845, Toogood. P., WO0119825, Toogood P., WO0138315, Reich S. H., WO0179198, Webster, K. U.S. Pat. No. 6,262,096.

For reviews of compounds inhibiting the Cdk4/cyclin D pathway see: Harris, W. and Wilkinson, S., *Emerging Drugs.* 2000, 5, 287-297; Dumas, J., *Exp. Opin. Ther. Patents.* 2001, 11, 405-429; Sielecki T., et. al., *J. Med. Chem.*, 2000, 43, 1-18. WO 99/21845, 6,569,878 B1, 2003/0220326 A1, and WO 2003011843 A1, all of which are related, disclose 4-aminothiazoles of general formula

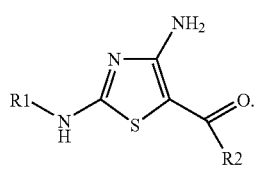

These compounds are stated to be inhibitors of cyclin-dependent kinases.

SUMMARY OF THE INVENTION

The present invention relates to novel 4-aminothiazole derivatives of the formula

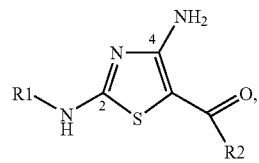

wherein $R^1$ is selected from the group lower alkyl substituted by aryl,

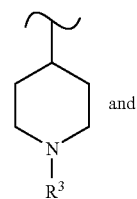

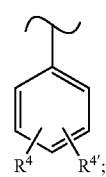

$R^2$ is selected from the group aryl, heteroaryl, cycloalkyl and heterocycle, wherein each may be substituted by up to four substituents independently selected from the group
  lower alkyl,
  halogen,
  $OR^5$,
  $NH_2$, and
  $NO_2$;
$R^3$ is selected from the group
  H,
  lower alkyl,
  $CO_2R^6$,
  $C(O)R^6$,
  $SO_2R^6$, and
  $SO_2NR^5R^6$;
$R^4$ and $R^{4'}$ are each independently selected from the group
  H,
  lower alkyl optionally substituted by oxo, $CO_2R^6$, $OR^6$ and/or $NH_2$,
  $S(O)_nR^7$,
  $OR^8$,
  $NR^5R^6$ and
  $CO^2R^6$;
$R^5$ and $R^6$ are each independently selected from the group
  H,
  N,
  lower alkyl,
  lower alkyl substituted by oxo, $CO_2R^9$, $OR^9$, and $NR^{10}R^{11}$,
  aryl, which optionally may be substituted by halogen heteroaryl, N-aryl, wherein the aryl group is optionally substituted by (h) one or more halogen substituents, and
aryl substituted by halogen or $CF_3$;
$R^7$ is lower alkyl or aryl;
$R^8$ is selected from the group H,
lower akyl, and
lower alkyl substituted by $NR^5R^6$;
$R^9$ is selected from the group H and lower alkyl;
$R^{10}$ and $R^{11}$ are each independently selected from H and lower alkyl;
and n is 0, 1 or 2;
or the pharmaceutically acceptable salts or esters thereof.

These compounds inhibit cyclin-dependent kinases. These compounds and their pharmaceutically acceptable salts and esters have antiproliferative activity and are useful in the treatment or control of cancer, in particular solid tumors.

The present invention also relates to pharmaceutical compositions comprising one or more compounds of the invention, or a pharmaceutically acceptable salt or ester thereof, and a pharmaceutically acceptable carrier or excipient.

The present invention further relates to a method for treating or controlling cancer, more particularly the treatment or control of a solid tumor, most particularly to the treatment or control of breast, lung and colon and prostate tumors by administering to a patient in need of such therapy a therapeutically effective amount of a compound of formula I, or a pharmaceutically salt or ester thereof.

Finally, this invention also relates to novel intermediate compounds useful in the preparation of a compound of formula I.

DETAILED DESCRIPTION OF THE INVENTION

Definitions

As used herein, the following terms shall have the following definitions.

"Aryl" means a monovalent, monocyclic or bicyclic, aromatic carbocyclic hydrocarbon radical, preferably a 6-10 membered aromatic ring system. Preferred aryl groups include, but are not limited to, phenyl, naphthyl, tolyl and xylyl.

"Cycloalkyl" means a non-aromatic, partially or completely saturated monovalent cyclic hydrocarbon radical containing 3 to 8 atoms. Examples of cycloalkyl groups include cyclopropyl, cyclobutyl, cyclopentyl and cyclohexyl.

"Effective amount" means an amount that is effective to prevent, alleviate or ameliorate symptoms of disease or prolong the survival of the subject being treated.

"Halogen" means fluorine, chlorine, bromine or iodine, preferably fluorine or chlorine.

"Hetero atom" means an atom selected from N, O and S.

"Heteroaryl" means an aromatic heterocyclic ring system containing up to two rings. Preferred heteroaryl groups include, but are not limited to, thienyl, furyl, indolyl, pyrrolyl, pyridinyl, pyridine, pyrazinyl, oxazolyl, thiaxolyl, quinolinyl, pyrimidinyl, imidazole, benzofuran and tetrazolyl.

"Heterocycle" or "heterocyclyl" means a saturated or partially unsaturated, non-aromatic cyclic radical of 3 to 8 ring atoms in which from one to 3 ring atoms are hetero atoms selected from nitrogen, oxygen, S(O)n (where n is an integer from 0 to 2), or a combination thereof, the remaining ring atoms being C. Examples of preferred heterocycles are piperidine, piperazine, pyrrolidine, morpholine, indoline, tetrahydropyranyl, thiomorpholino, pentamethylene sulfide, and pentamethylene sulfone.

"$K_i$" refers to a measure of the thermodynamic binding of the ligand/inhibitor (that is, a compound according to the invention) to the target protein. $K_i$ can be measured, inter alia, as is described in Example 18, infra.

"Lower alkyl" alone or in conjunction with another term, e.g. lower alkyl-heterocycle, denotes a straight-chain or branched saturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl, hexyl and the like.

"Oxo" means=O.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid. Examples of ester groups which are cleaved (in this case hydrolyzed) in vivo to the corresponding carboxylic acids ($R^{40}C(=O)OH$) are lower alkyl esters which may be substituted with $NR^{41}R^{42}$ where $R^{41}$ and $R^{42}$ are lower alkyl, or where $NR^{41}R^{42}$ taken together form a monocyclic aliphatic heterocycle, such as pyrrolidine, piperidine, morpholine, N-methylpiperazine, etc.; acyloxyalkyl esters of the formula $R^{40}C(=O)OCHR^{43}OC(=O)R^{44}$ where $R^{43}$ is hydrogen or methyl, and $R^{44}$ is lower alkyl or cycloalkyl; carbonate esters of the formula $R^{40}C(=O)OCHR^{43}OC(=O)OR^{45}$ where $R^{43}$ is hydrogen or methyl, and $R^{45}$ is lower alkyl or cycloalkyl; or aminocarbonylmethyl esters of the formula $R^{40}C(=O)OCH_2C(=O)NR^{41}R^{42}$ where $R^{41}$ and $R^{42}$ are hydrogen or lower alkyl, or where $NR^{41}R^{42}$ taken together form a monocyclic aliphatic heterocycle, such as pyrrolidine, piperidine, morpholine, N-methylpiperazine, etc. As used herein, $R^{40}$ has the same definition as $R^2$, $R^3$, $R^4$ and $R^{4'}$.

Examples of lower alkyl esters are the methyl, ethyl, and n-propyl esters, and the like. Examples of lower alkyl esters substituted with $NR^{41}R^{42}$ are the diethylaminoethyl, 2-(4-morpholinyl)ethyl, 2-(4-methylpiperazin-1-yl)ethyl esters, and the like. Examples of acyloxyalkyl esters are the pivaloxymethyl, 1-acetoxyethyl, and acetoxymethyl esters. Examples of carbonate esters are the 1-(ethoxycarbonyloxy)ethyl and 1-(cyclohexyloxycarbonyloxy)ethyl esters. Examples of aminocarbonylmethyl esters are the N,N-dimethylcarbamoylmethyl and carbamoylmethyl esters.

Further information concerning examples of and the use of esters for the delivery of pharmaceutical compounds is available in Design of Prodrugs. Bundgaard H ed. (Elsevier, 1985). See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluene sulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options.

"Therapeutically effective amount" means an amount of at least one compound of Formula I, or a pharmaceutically acceptable salt or ester thereof, that significantly inhibits proliferation and/or prevents differentiation of a human tumor cell, including human tumor cell lines.

In one embodiment, the present invention relates to compounds of formula I

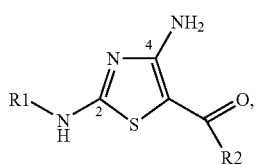

I or the pharmaceutically acceptable salts or esters thereof, wherein $R^1$ and $R^2$ are as defined above.

In a preferred embodiment of the compounds of formula I, $R^2$ is phenyl, preferably phenyl substituted by halogen, most preferably F, and $OR^5$ wherein $R^5$ is lower alkyl. In a most preferred embodiment, $R^2$ is phenyl substituted by one or two F molecules and one $OR^5$ group wherein $R^5$ is lower alkyl, preferably methyl.

In another preferred embodiment of the compounds of formula I, $R^2$ is as defined above and $R^1$ is

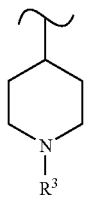

wherein
  $R^3$ is selected from the group
  H,
  $CO_2R^6$,
  $C(O)R^6$,
  $SO_2R^6$, and
  $SO_2NR^5R^6$;
  $R^5$ and $R^6$ are each independently selected from the group
  H, and lower alkyl;

or the pharmaceutically acceptable salts or esters thereof.
Examples of compounds of formula I above include but are not limited to:
4-[4-Amino-5-(3-fluorobenzoyl)thiazol-2-ylamino]piperidine-1-carboxylic acid tert-butyl ester, 4-[4-Amino-5-(3-fluoro-4-methoxybenzoyl)thiazol-2-ylamino]piperidine-1-carboxylic acid tert-butyl ester,
4-[4-Amino-5-(2, 3-difluoro-6-methoxybenzoyl)thiazol-2-ylamino]piperidine-1-carboxylic acid tert-butyl ester,
[4-Amino-2-(piperidin-4-ylamino)thiazol-5-yl]-(3-fluorophenyl)methanone, [4-Amino-2-(piperidin-4-ylamino)thiazol-5-yl]-(3-fluoro-4-methoxyphenyl)methanone,
[4-Amino-2-(piperidin-4-ylamino)thiazol-5-yl]-(2, 3-difluoro-6-methoxyphenyl)methanone,
1-[4-[4-Amino-5-(3-fluorobenzoyl)thiazol-2-ylamino]piperidin-1-yl]ethanone, [4-Amino-2-(1-methanesulfonylpipeidin-4-ylamino)thiazol-5-yl]-(3-fluoro-phenyl)methanone),
1-[4-[4-amino-5-(3-fluoro4-methoxybenzoyl)thiazol-2-ylamino]piperidin-1-yl]ethanon,
[4-Amino-2-(1-methanesulfonylpiperidin-4-ylamino)thiazol-5-yl]-(3-fluoro-4-methoxy-phenyl)methanone,
4-[4-Amino-5-(3-fluoro-4-methoxybenzoyl)thiazol-2-ylamino]piperidine-1-sulfonic acid dimethylamide,
[4-Amino-2-(1-methanesulfonylpiperidin-4-ylamino)thiazol-5-yl]-(2,3-difluoro-6-methoxyphenyl)methanone, and
[4-Amino-2-(1-methanesulfonyl-piperidin-4-ylamino)thiazol-5-yl]-(2,6-difluorophenyl)methanone.

In another embodiment of the invention, $R^1$ is

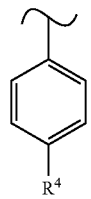

wherein $R^4$ is $S(O)_nR^7$, wherein $R^7$ is lower alkyl, preferably methyl. Most preferably $R^4$ is $—S(O)_2CH_3$.

Examples of compounds of formula I above include: [4-Amino-2-(4-methanesulfonylphenylamino)thiazol-5-yl]-(2,3-difluoro-6-methoxyphenyl)methanone.

The compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formula above In another embodiment, examples of compounds of this invention include but are not limited to:

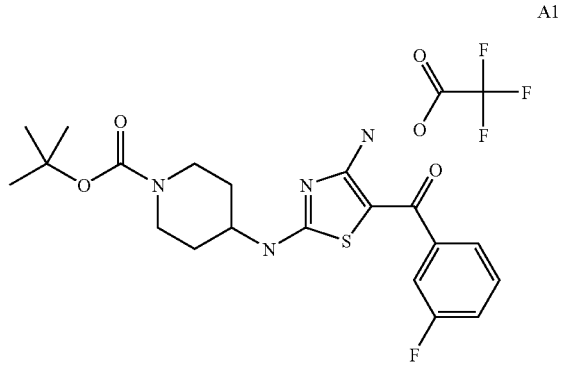

A1

-continued
A2
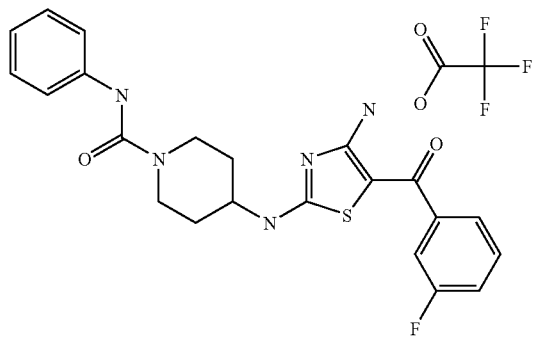
A3
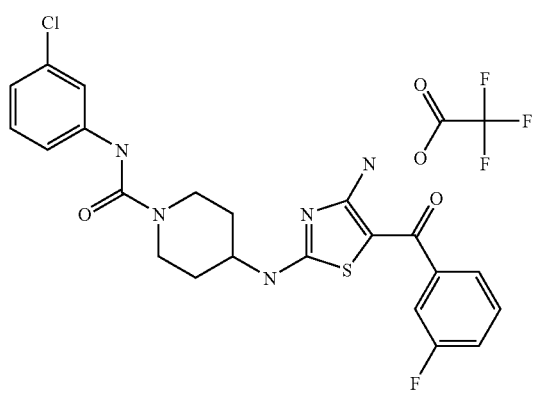
A4
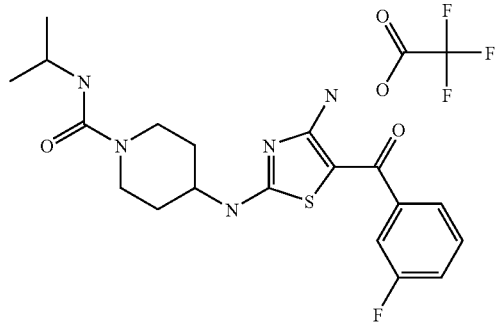
A5
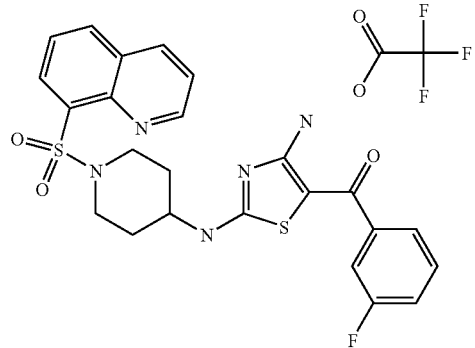
-continued
A6
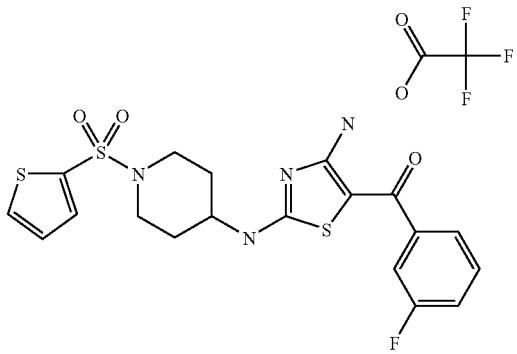
A7
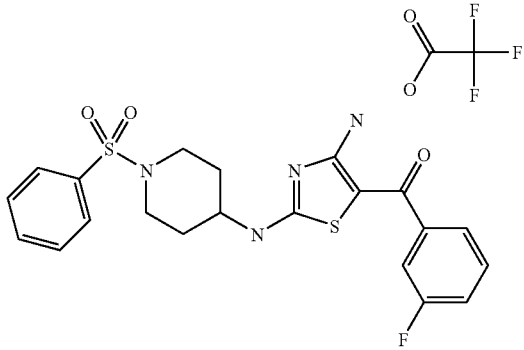
A8
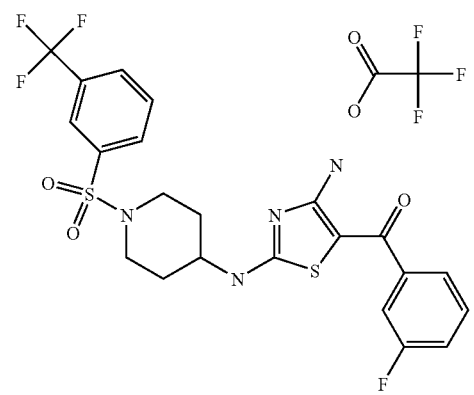
A9
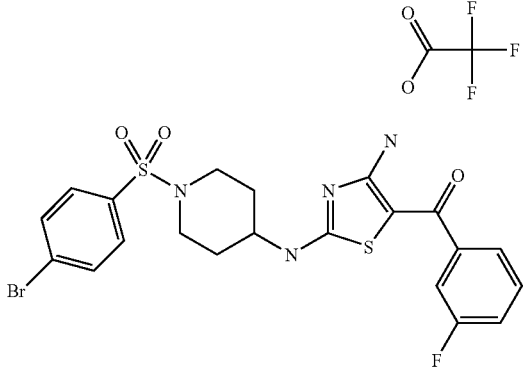

-continued
A10
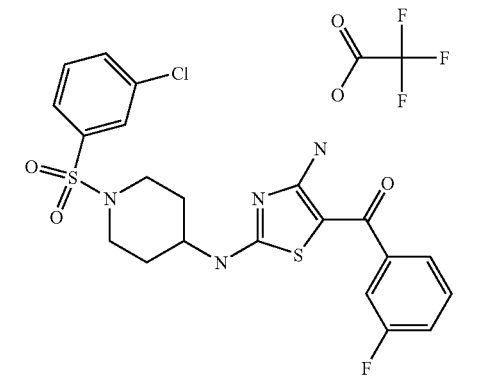
A11
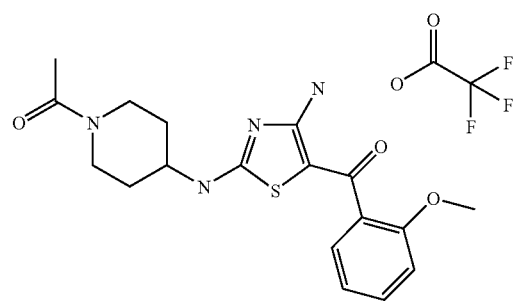
A12
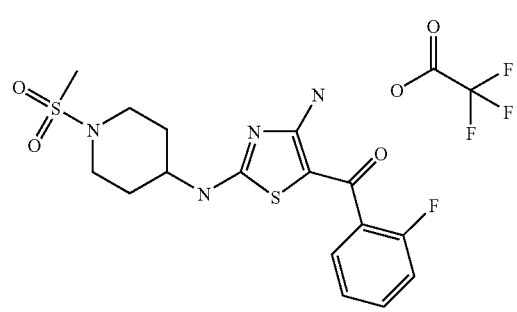
A13
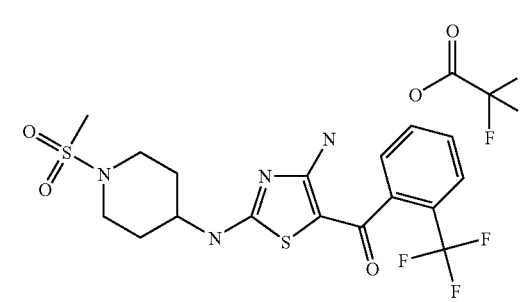
A14
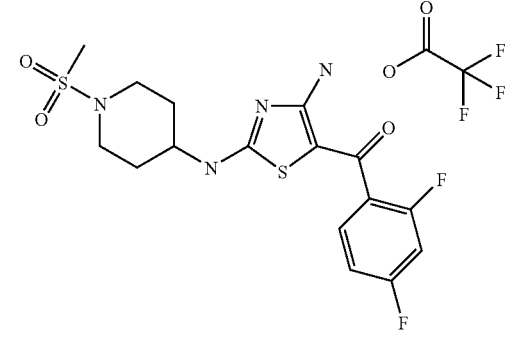
-continued
A15
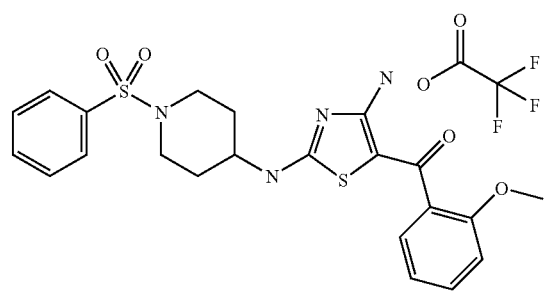
A16
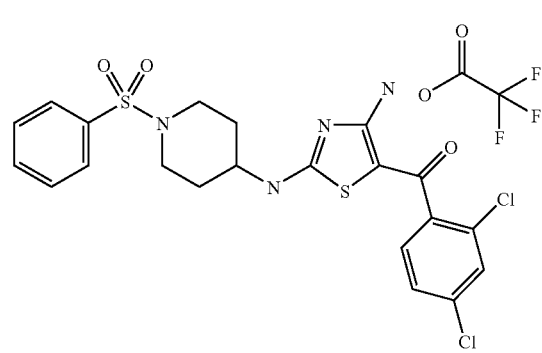
A17
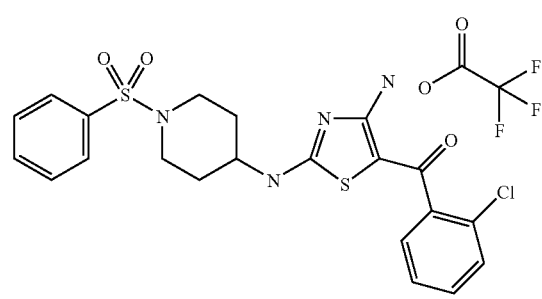
A18
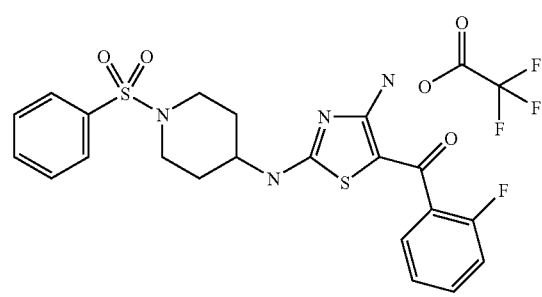
A19
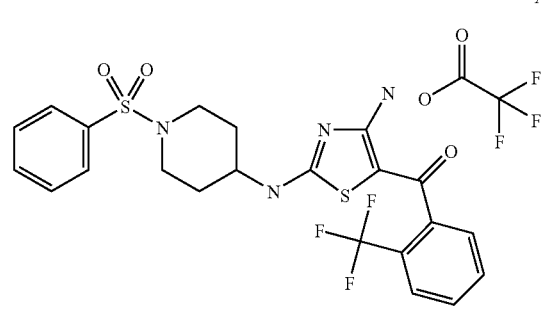

-continued
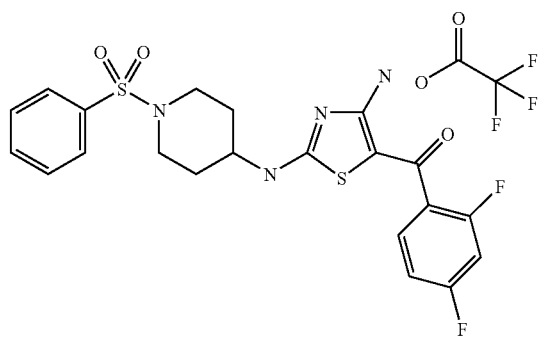
A20
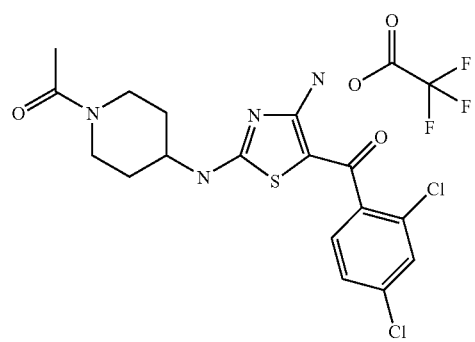
A21
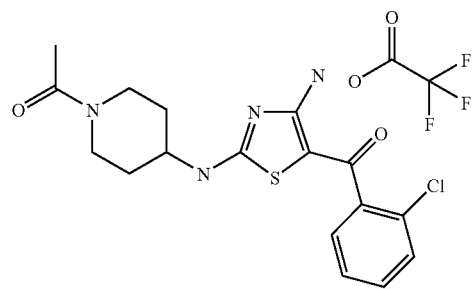
A22
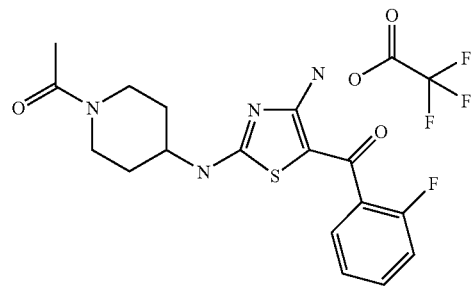
A23
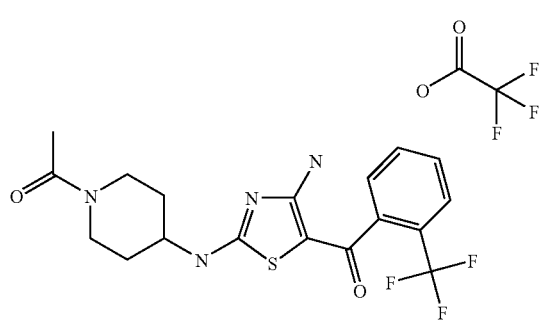
A24
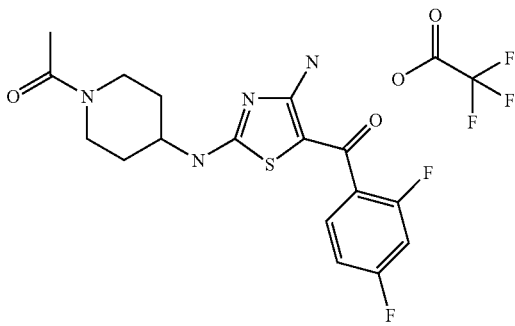
A25
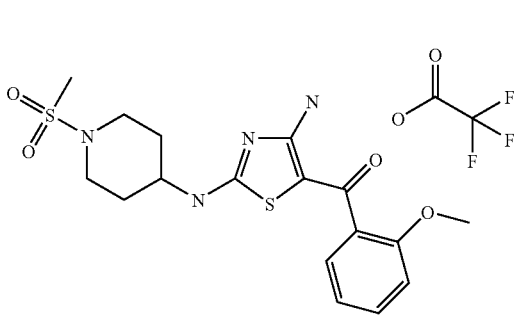
A26
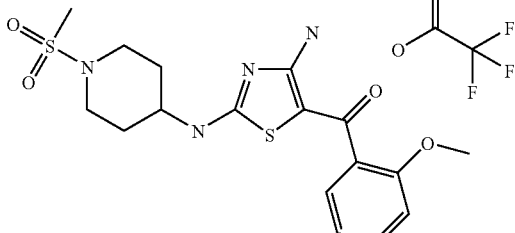
A27
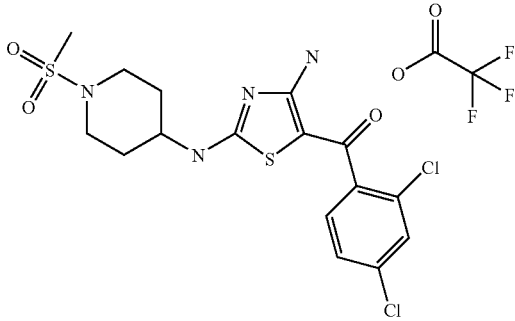
A28
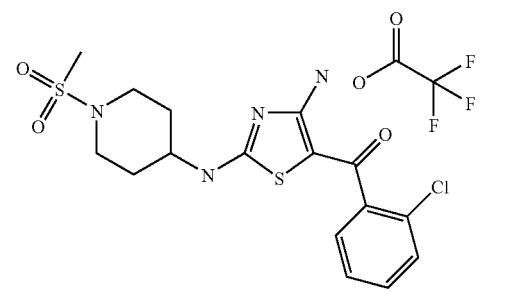
A29

-continued

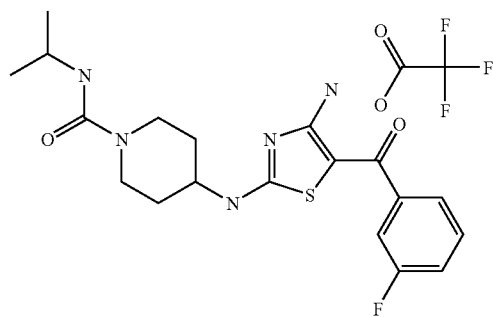
A30

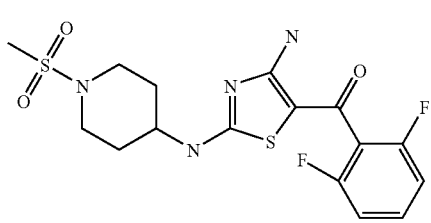
A31

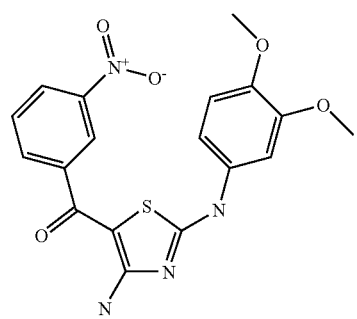
A32

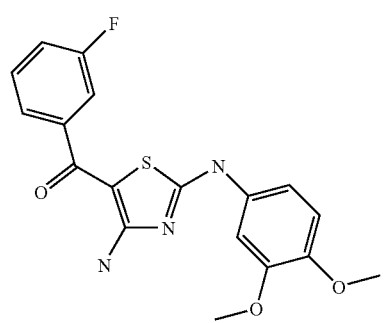
A33

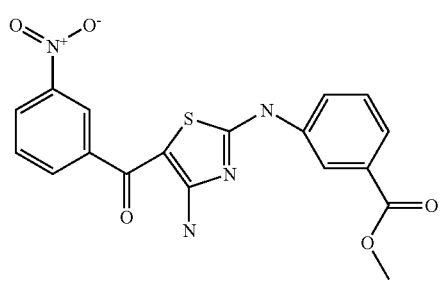
A34

-continued

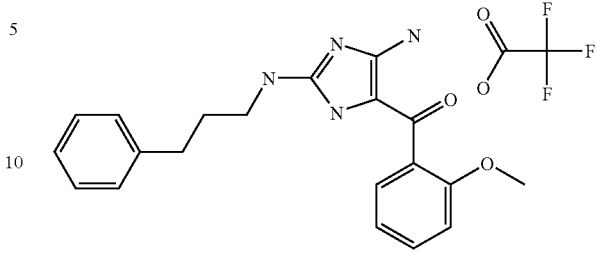
A35

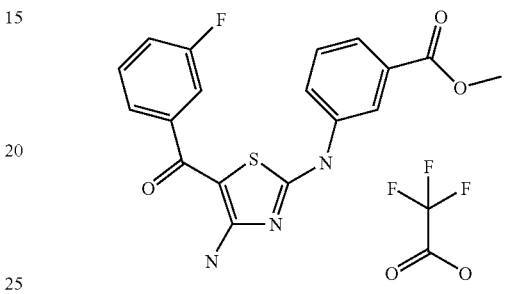
A36

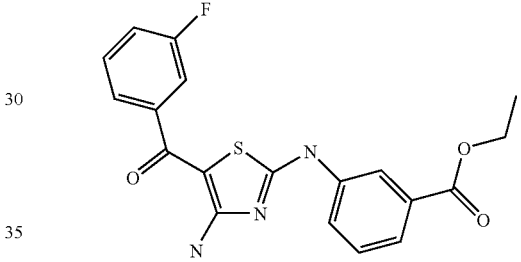
A37

General Synthesis of Compounds According to the Invention

The compounds of the present invention can be prepared by any conventional means. Suitable processes for synthesizing these compounds are provided in the examples. Generally, compounds of formula I can be prepared according to one of the below described synthetic routes.

Ring Formation

Compounds of the invention can be prepared by the alkylation and cyclization of a number of thiourea derivatives, as shown in Scheme III, using reactions that are known. Among the thiourea derivatives that can be used are nitroamidinothioureas (Binu, R. et al. *Org. Prep. Proced. Int* 1998, 30, 93-96); 1-[(arylthiocarbamoyl)amino]-3,5-dimethylpyrazoles (Jenardanan, G. C. et al. *Synth. Commun.* 1997, 27, 3457-3462); and N-(aminoiminomethyl)-N'-phenylthioureas (Rajasekharan, K. N. et al. *Synthesis* 1986, 353-355).

Another thiourea derivative that can be used for the preparation of compounds of the invention by alkylation and cyclization is N-cyanothiourea (Gewald, K. et al. *J. Prakt. Chem.* 1967, 97-104). For example, pursuant to Scheme III below, an N-cyanothiourea of formula 6 can be reacted with a halomethylketone, such as a bromomethylketone of formula 4, at a temperature between around room temperature and around 65° C., to give a compound of formula 7. When not commercially available, the starting materials of formulae (2) and (4) are cited under the individual examples.

Scheme I

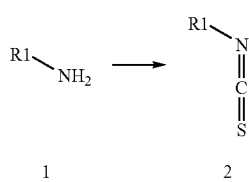

Scheme II

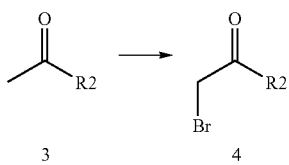

Scheme III

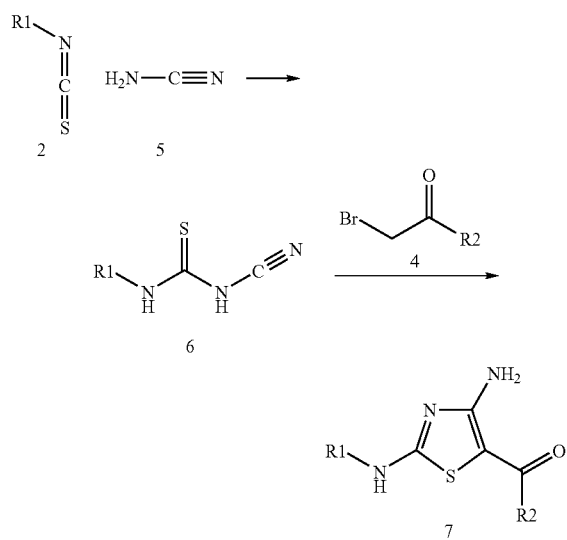

Alternatively, the compounds of the invention are also conveniently prepared by reaction of a resin-bound substituted (aminothioxomethyl) carbamimidothioic acid methyl ester of formula 9 with a bromomethyl ketone of formula 4 as shown in Scheme IV below.

Scheme IV

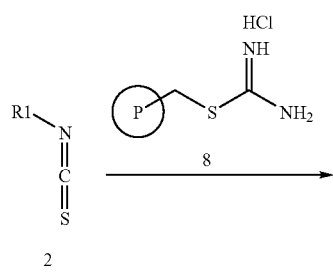

-continued

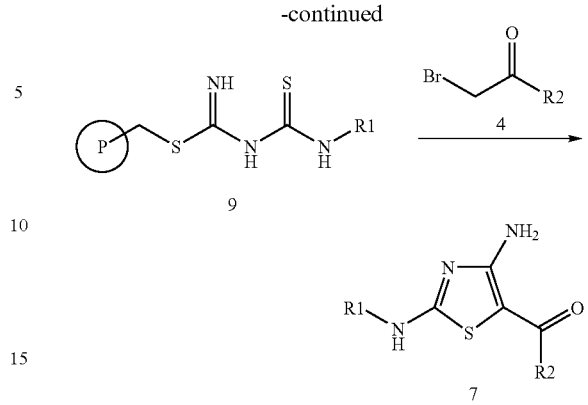

The resin-bound thiourea derivative of formula 9 can be made by any conventional procedure known to one skilled in the art of organic synthesis. For example, it can be conveniently prepared by the reaction of a resin-bound thiouronium salt of formula 8 with an isothiocyanate of formula 2 in the presence of a base, such as a tertiary amine (e.g., triethylamine or diisopropylethylamine) in an inert solvent, such as a polar aprotic solvent (e.g., N,N-dimethylformamide). The reaction is conveniently carried out at a temperature around room temperature. The resin-bound thiourea derivative of formula 9 is then converted to the product of formula 7 by treatment with a halomethylketone (for example, a bromomethylketone of formula 4) in a suitable inert solvent such as a polar aprotic solvent (e.g., N,N-dimethylformamide) at a temperature around room temperature.

Separating a Mixture of Stereoisomers into the Optically Pure Stereoisomers (When Compound of Formula I is Chiral)

The optional separation of isomeric structures of formula I can be carried out according to known methods such as for example resolution or chiral high pressure liquid chromatography (also known as chiral HPLC). Resolution methods are well known, and are summarized in "Enantiomers, Racemates, and Resolutions" (Jacques, J. et al. John Wiley and Sons, NY, 1981). Methods for chiral HPLC are also well known, and are summarized in "Separation of Enantiomers by Liquid Chromatographic Methods" (Pirkle, W. H. and Finn, J. in "Asymmetric Synthesis", Vol. 1, Morrison, J. D., Ed., Academic Press, Inc., NY 1983, pp. 87-124).

Converting a Compound of Formula I that Bears a Basic Nitrogen into a Pharmaceutically Acceptable Acid Addition Salt The optional conversion of a compound of formula I that bears a basic nitrogen into a pharmaceutically acceptable acid addition salt can be effected by conventional means. For example, the compound can be treated with an inorganic acid such as for example hydrochloric acid, hydrobromic acid, sulfuric acid, nitric acid, phosphoric acid, or with an appropriate organic acid such as acetic acid, citric acid, tartaric acid, methanesulfonic acid, p-toluene sulfonic acid, or the like.

Converting a Compound of Formula I that Bears a Carboxylic Acid Group into a Pharmaceutically Acceptable Alkali Metal Salt The optional conversion of a compound of formula I that bears a carboxylic acid group into a pharmaceutically acceptable alkali metal salt can be effected by conventional means.

For example, the compound can be treated with an inorganic base such as lithium hydroxide, sodium hydroxide, potassium hydroxide, or the like.

Converting a Compound of Formula I that Bears a Carboxylic Acid Group into a Pharmaceutically Acceptable Ester The optional conversion of a compound of formula I that bears a carboxylic acid group into a pharmaceutically acceptable ester can be effected by conventional means. The conditions for the formation of the ester will depend on the stability of the other functional groups in the molecule to the reaction conditions. If the other moieties in the molecule are stable to acidic conditions, the ester may be conveniently prepared by heating in a solution of a mineral acid (e.g., sulfuric acid) in an alcohol. Other methods of preparing the ester, which may be convenient if the molecule is not stable to acidic conditions include treating the compound with an alcohol in the presence of a coupling agent and in the optional presence of additional agents that may accelerate the reaction. Many such coupling agents are known to one skilled in the art of organic chemistry. Two examples are dicyclohexylcarbodiimide and triphenylphosphine/dienthyl azodicarboxylate. In the case where dicyclohexylcarbodiimide is used as the coupling agent, the reaction is conveniently carried out by treating the acid with the alcohol, dicyclohexylcarbodiimide, and the optional presence of a catalytic amount (0-10 mole %) of N,N-dimethylaminopyridine, in an inert solvent such as a halogenated hydrocarbon (e.g., dichloromethane) at a temperature between about 0 degrees and about room temperature, preferably at about room temperature. In the case where triphenylphosphine/diethyl azodicarboxylate is used as the coupling agent, the reaction is conveniently carried out by treating the acid with the alcohol, triphenylphosphine and diethyl azodicarboxylate, in an inert solvent such as an ether (e.g., tetrahydrofuran) or an aromatic hydrocarbon (e.g., benzene) at a temperature between about 0 degrees and about room temperature, preferably at about 0 degrees.

Compositions/Formulations

In an alternative embodiment, the present invention includes pharmaceutical compositions comprising at least one compound of formula I, or a pharmaceutically acceptable salt or ester thereof and an a pharmaceutically acceptable excipient and/or carrier.

These pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, and/or the salts or esters thereof, may be manufactured in a manner that is known in the art, e.g. by means of conventional mixing, encapsulating, dissolving, granulating, emulsifying, entrapping, drageemaking, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

Dosages

As mentioned above, the compounds of the present invention, including the compounds of formula I, are useful in the treatment or control of cell proliferative disorders, including chemoprevention of cancer. Chemoprevention is defined as inhibiting the development of invasive cancer by either blocking the initiating mutagenic event or by blocking the progression of pre-malignant cells that have already suffered an insult of inhibiting tumor relapse. These compounds and formulations containing said compounds are particularly useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Combinations

The compounds of this invention may be used in combination (administered in combination or sequentially) with known anti-cancer treatments such as radiation therapy or with cytostatic or cytotoxic agents, such as for example, but not limited to, DNA interactive agents, such as cisplatin or doxorubicin; topoisomerase II inhibitors such as etoposide: topoisomerase I inhibitors such as CPT-11 or topotecan; tublin interacting agents, such as paclitaxel, docetaxel or epothilones; hormonal agents such as tamoxifen: thymidilate synthase inhibitors, such as 5-fluorouracil; and anti-metabolites such as methotrexate. Compounds of formula I may also be useful in combination with modulators of p53 transactivation.

If formulated as a fixed dose, the above-described combination products include the compounds of this invention within the dosage range described above and the other pharmaceutically active agent or treatment within its approved dose range. For example, an early cdk1 inhibitor olomucine has been found to act synergistically with well known cytotoxic agents in inducing apoptosis. (*J. Cell Sci.*, 1995, 108, 2897-2904). Compounds of formula I may also be administered sequentially with known anticancer or cytotoxic agents when concomitant administration or a combination is inappropriate. This invention is not limited in the sequence of administration: compounds of formula I may be administered either prior to or after administration of the known anticancer or cytotoxic agent. For example, the cytotoxic activity of the cdk inhibitor flavopiridol is affected by the sequence of administration with anticancer agents. (*Cancer Research*, 1997, 57, 3375).

EXAMPLES

The following examples illustrate preferred methods for synthesizing and using the compounds and formulations of the present invention. These examples and preparations are illustrative and are not intended to be limiting. It should be understood that there may be other embodiments which fall within the spirit and scope of the invention as defined by the claims appended hereto.

Example 1

4-lsothiocyanatopiperidine-1-carboxylic acid tert-butyl ester (32468-246)

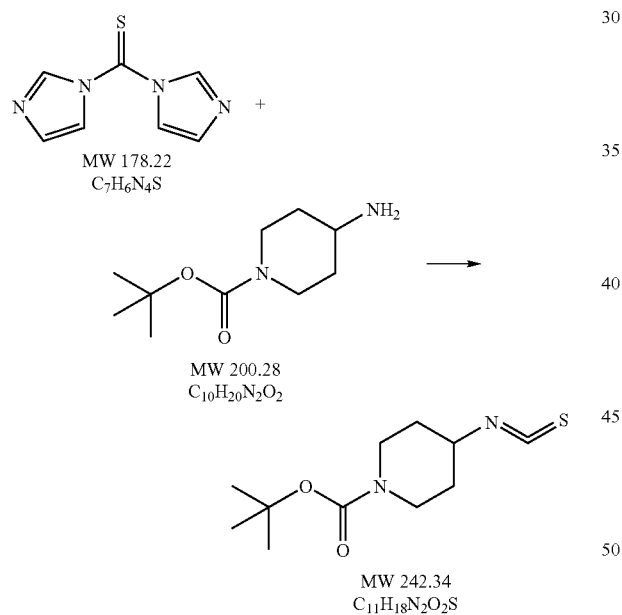

4-Aminopiperidine-1-carboxylic acid tert-butyl ester (5.0 g, 25 mmol) (Astatech, Inc) was dissolved in dimethylformamide (120 mL) and cooled to −15° C. Thiocarbonyidiimidazole (4.8 g, 27 mmol) (Aldrich) in dimethylformamide (100 mL) was added slowly at below −10° C. The mixture was stirred at room temperature for 14 h. All solvent was removed under vacuum and the residue was dissolved in methylene chloride (200 mL) and washed 2× water. The solvent was removed and the residue was triturated with hexane. This was filtered and the solution treated with Norite and filtered through celite. Removal of solvent gave 4-isothiocyanatopiperidine-1-carboxylic acid tert-butyl ester (5.7 g, 94% yield) as oil. LR-MS-EI(+): Compatible with 242 MW.

Example 2

2-Bromo-1-(3-fluorophenyl)ethanone (32468-142)

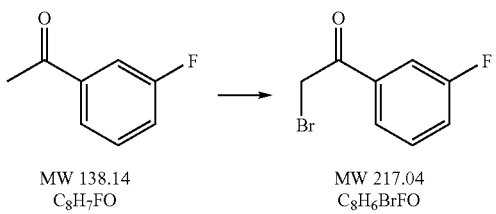

A solution of 1-(3-fluorophenyl)ethanone (14.0 g, 100 mmol) (Aldrich) in dioxane (250 mL) at 12-15° C. was treated with a solution of bromine (17 g, 105 mmol) in dioxane (120 mL) drop wise over 0.5 h. This was stirred for 15 min and most of the solvent removed. The residue was taken up in hexane (200 mL), washed 2× water, and dried (MgSO$_4$). Solvent was removed to give 2-bromo-1-(3-fluorophenyl) ethanone. $^1$H NMR (CDCl3), 300 MHz) δ3.71 (s, 2H, CH$_2$), 7.30-7.77(m, 4H, Aromatic).

Example 3

4-[4-Amino-5-(3-fluorobenzoyl)thiazol-2-ylamino] piperidine-1-carboxylic acid tert-butyl ester (32468-249-1)

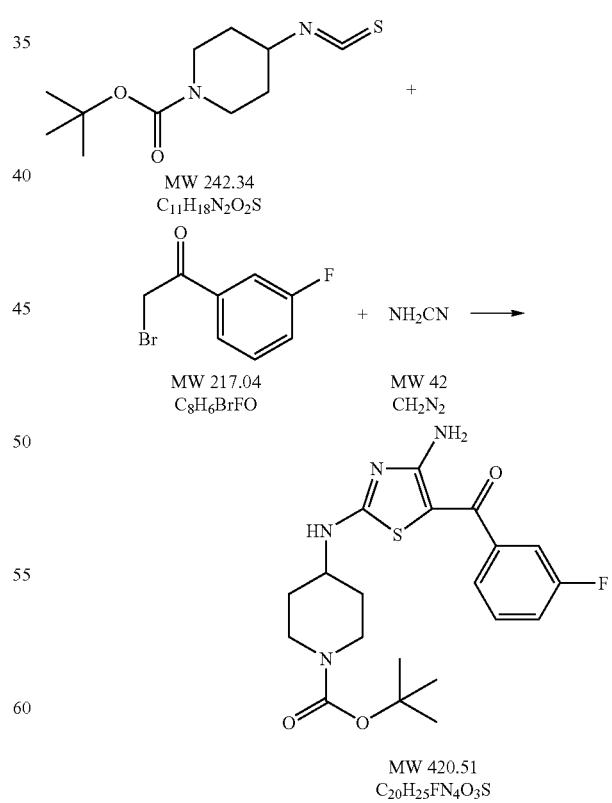

At 20° C., a mixture of 4-isothiocyanatopiperidine-1-carboxylic acid tert-butyl ester (2.4 g, 10 mmol) (Example 1) and cyanamide (0.42 g, 10 mmol) (Aldrich) in tert-butanol (5 mL) and acetonitrile (35 mL) was treated with potassium tert-butoxide (1.0 M/THF, 10 mL, 10 mmol, Aldrich) for 15 min. 2-bromo-1-(3-fluorophenyl)ethanone (2.0 g, 9.2 mmol)(Example 2) was added and the suspension was stirred for 2 h. Solvent was removed and the solid residue purified by silica gel chromatography (60%-70% ethyl acetate/hexane) to give 2.4 g (57% yield) of 4-[4-amino-5-(3-fluorobenzoyl)thiazol-2-ylamino]piperidine-1-carboxylic acid tert-butyl ester. $^1$H NMR (DMSO$_{d6}$, 300 MHz) δ1.36 (m, 2H, NCH$_2$), 1.41 (s, 9H, 3CH$_3$), 1.88 (m, 2H, NCH$_2$), 2.88 (brd, 2H, NCH$_2$), 3.6-4.0 (m, 1H, CH), 3.87 (m, 2H, NCH$_2$), 7.31 (t, 1H, Aromatic), 7.38 (d, 1H, Aromatic), 7.48 (t, 1H, Aromatic), 7.51 (q, 1H, Aromatic), 8.01 (brd, 1H, NH), 8.48 (brd, 1H, NH), 8.48 (brd, 1H, NH), 8.70 (brd, 1H, NH).

Example 4

4-4-Amino-5-(3-fluoro-4-methoxybenzoyl)thiazol-2-ylamino]piperidine-1-carboxylic acid tert-butyl ester (32468-247)

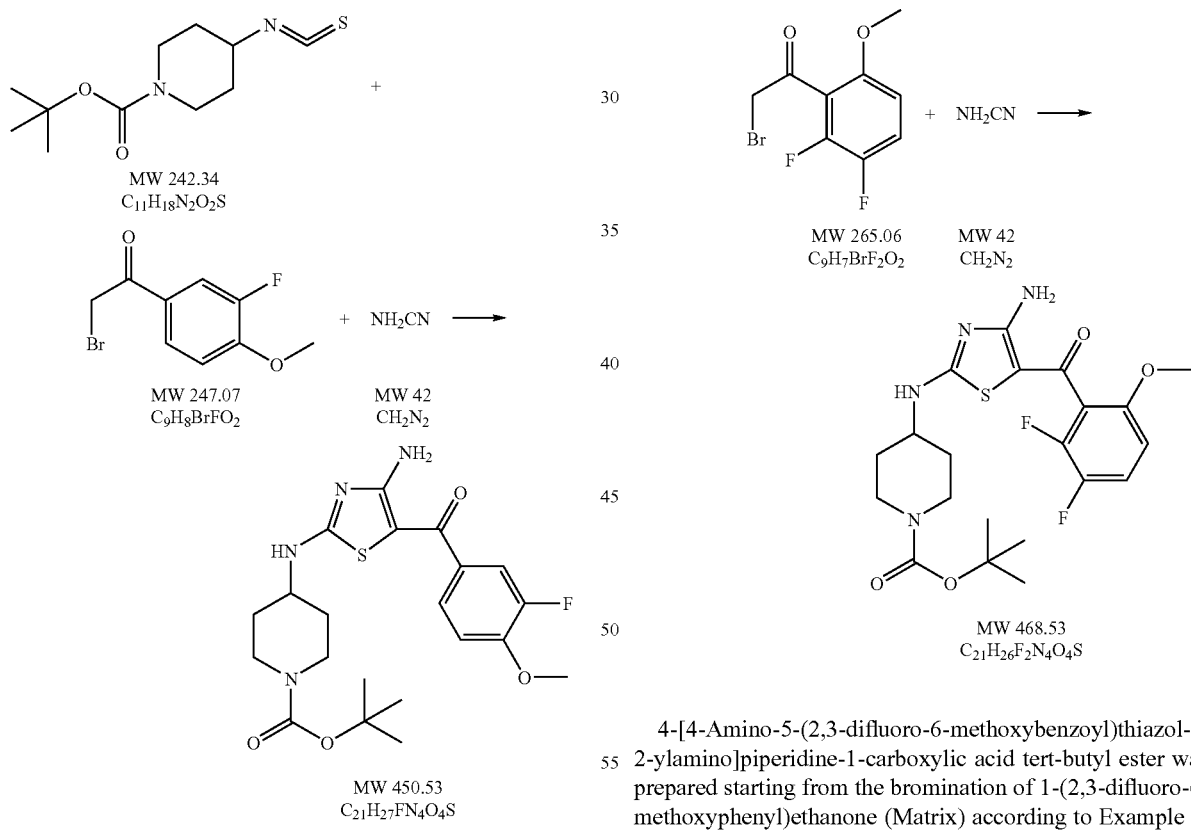

4-[4-Amino-5-(3-fluoro4-methoxybenzoyl)thiazol-2-ylamino]piperidine-1-carbosylic acid tert-butyl ester was prepared starting from the bromination of 1-(3-fluoro-4-methoxyphenyl)ethanone (Aldrich) according to Example 2, followed by the cyclization described in Example 3 to give 4-[4-amino-5-(3-fluoro-4-methoxybenzoyl)thiazol-2-ylamino]piperidine-1-carboxylic acid tert-butyl ester. $^1$H NMR (DMSO$_{d6}$, 300 MHz) δ1.37 (m, 2H, CH$_2$), 1.41 (s, 9H, 3CH$_3$), 1.80 (m, 2H, CH$_2$), 2.78 (brd, 2H, NCH$_2$), 3.32 (m, 2H, NCH$_2$), 3.6-4.0 (broad, 1H CH), 3.85 (m, 3H, OCH$_3$), 7.22 (t, 1H, Aromatic), 7.45 (d, 1 H, Aromatic), 7.48 (m, 1H, Aromatic), 7.94 (brd, 1H, NH), 8.45 (brd, 1H, NH), 8.65 (brd, 1H, NH). HRMS: (M+H)+: observed: 451.1813; calcd for 451.1810.

Example 5

4-[4-Amino-5-(2,3-difluoro-6-methoxybenzoyl)thiazol-2-ylamino]piperidine-1-carboxylic acid tert-butyl ester (33245-287-A)

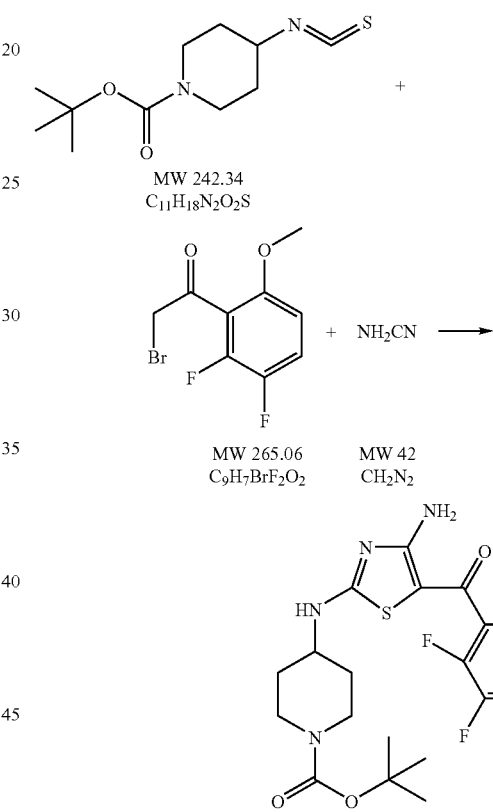

4-[4-Amino-5-(2,3-difluoro-6-methoxybenzoyl)thiazol-2-ylamino]piperidine-1-carboxylic acid tert-butyl ester was prepared starting from the bromination of 1-(2,3-difluoro-6-methoxyphenyl)ethanone (Matrix) according to Example 2, followed by the cyclization as described in Example 3 to give 4-[4-Amino-5-(2,3-difluoro-6-methoxybenzoyl)thiazol-2-ylamino]piperidine-1-carboxylic acid tert-butyl ester. $^1$H NMR (DMSO$_{-d6}$, 300 MHz) δ1.48 (m, 2H, CH$_2$), 1.92 (m, 2H, CH$_2$), 2.55 (s, 9H, 3CH$_3$), 2.75 (m, 2H, CH$_2$), 3.39 (m, 2H, CH$_2$), 3.6-4.0 (broad, 1H, CH), 3.81(s, 3H, OCH$_3$), 6.92 (m, 1H, Aromatic), 7.50 (m, 1H, Aromatic), 7.6 (2× brd, 1H, NH), 7.8 (brd, 1H, NH), 7.99 (m, 1H,Aromatic), 9.0 (brd, 1H, NH). LR-MS-ES(±): Compatible with 468 MW.

Example 6

[4-Amino-2-(piperidin-4-ylamino)thiazol-5-yl]-(3-fluorophenyl)methanone (32468-251-1)

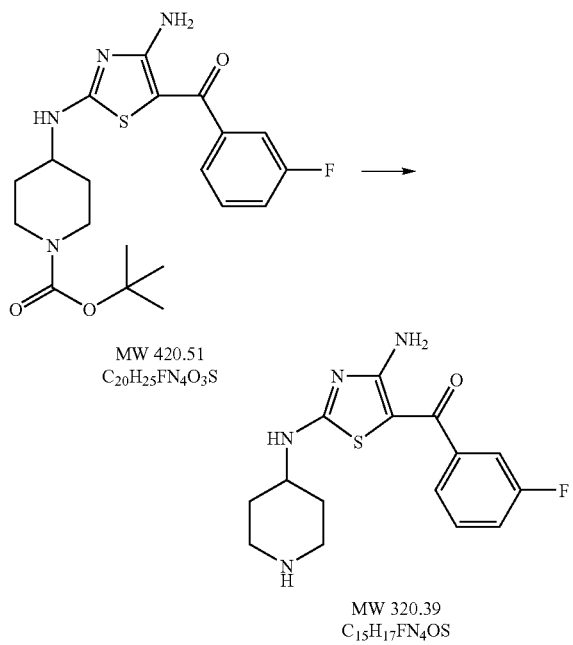

MW 420.51
C₂₀H₂₅FN₄O₃S

MW 320.39
C₁₅H₁₇FN₄OS

4-[4-Amino-5-(3-fluorobenzoyl)thiazol-2-ylamino]piperidine-1-carboxylic acid tert-butyl ester (0.82 g, 1.95 mmol) (Example 3) was dissolved in a mixture of trifluoroacetic acid (16 mL) and methylene chloride (30 mL). After 1 hr, all solvent was removed and the residue dissolved in methylene chloride (300 mL). This was washed with 10% Na$_2$CO$_3$ (50 mL), dried (Na$_2$SO$_4$) and concentrated to give a semi solid. This was triturated with ethyl ether and filtered to give 450 mg (72% yield) of [4-amino-2-(piperidin-4-ylamino)thiazol-5-yl]-(3-fluorophenyl)methanone. $^1$H NMR (DMSO$_{-d6}$, 300 MHz) δ1.38 (m, 2H, CH$_2$), 1.88 (m, 2H, CH$_2$), 2.95 (m, 2H, CH$_2$), 3.32 (brd, 2H, CH$_2$), 3.6-4.0 (broad, 1H, CH), 3.78 (s, 3H, OCH$_3$), 7.31 (t, 1H, Aromatic), 7.38 (d, 1H, Aromatic), 7.48 (t, 1H, Aromatic), 7.51 (q, 1H, Aromatic), 8.01 (brd, 1H, NH), 8.48 (brd, 1H, NH), 8.70 (brd, 1H, NH). LR-MS-ES(±): Compatible with 320 MW.

Example 7

[4-Amino-2-(piperidin-4-ylamino)thiazol-5-yl]-(3-fluoro-4-methoxyphenyl)methanone) (32468-248-1)

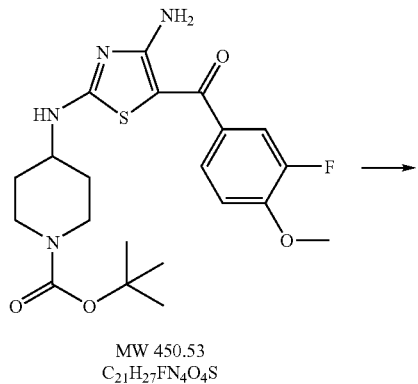

MW 450.53
C₂₁H₂₇FN₄O₄S

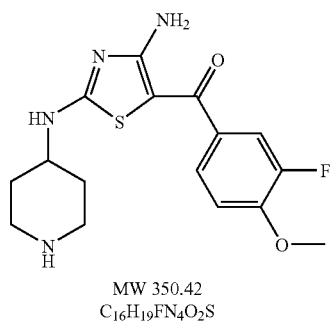

MW 350.42
C₁₆H₁₉FN₄O₂S

4-[4-Amino-5-(3-fluoro4-methoxybenzoyl)thiazol-2-ylamino]piperidine-1-carboxylic acid tert-butyl ester (0.30 g, 0.66 mmol) (Example 4) was deprotected in a manner described for Example 6 to give 220 mg (90% yield) of [4-amino-2-(piperidin-4-ylamino)thiazol-5-yl]-(3-fluoro-4-methoxyphenyl)methanone. $^1$H NMR (DMSO$_{-d6}$, 300 MHz) δ1.36 (m, 2H, CH$_2$), 1.75 (m, 2H, CH$_2$), 2.88 (brd, 2H, CH$_2$), 3.32 (m, 2H, CH$_2$), 3.2-3.4 (brd,1H, NCH), 3.78 (s, 3H, OCH$_3$), 7.23 (t, 1H, Aromatic), 7.48 (t, 1H, Aromatic), 7.62 (t, 1H, Aromatic), 8.01 (brd, 1H, NH), 8.48 (brd, 1H, NH), 8.70 (brd, 1H, NH). LR-MS-ES(±): Compatible with 350 MW.

Example 8

[4-Amino-2-(piperidin4-ylamino)thiazol-5-yl]-(2,3-difluoro-6-methoxyphenyl)methanone (33245-289-A)

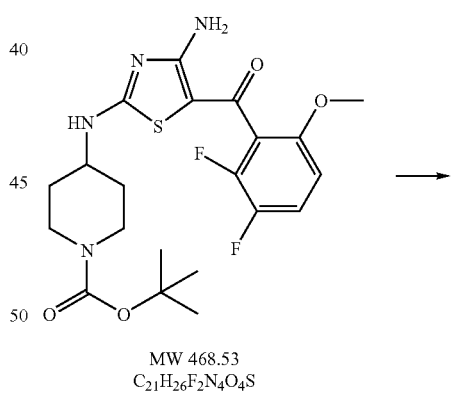

MW 468.53
C₂₁H₂₆F₂N₄O₄S

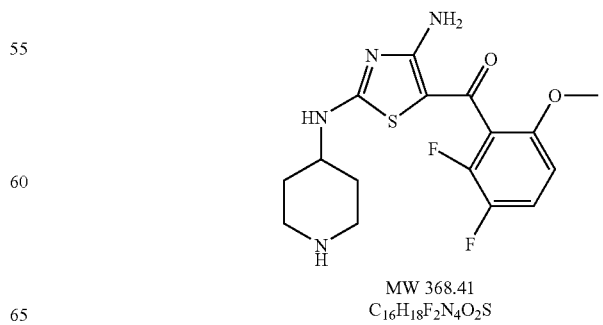

MW 368.41
C₁₆H₁₈F₂N₄O₂S

4-[4-Amino-5-(2,3-difluoro-6-methoxybenzoyl)thiazol-2-ylamino]piperidine-1-carboxylic acid tert-butyl ester (0.30 g, 0.64 mmol) (Example 5) was deprotected in a manner described for Example 6 to give 123 mg (52% yield) of [4-amino-2-(piperidin-4-ylamino)thiazol-5-yl]-(2,3-difluoro-6-methoxyphenyl)methanone. $^1$H NMR (DMSO$_{-d6}$, 300 MHz) δ1.38 (m, 2H, CH$_2$), 1.78 (m, 2H, CH$_2$), 2.91 (brd, 2H, CH$_2$), 3.35 (m, 3H, CH & NCH$_2$), 3.75 (s, 3H, OCH$_3$), 6.95 (m, 1H, Aromatic), 7.43 (m, 1H, Aromatic), 8.01 (brd, 1H, NH), 8.48 (brd, 1H, NH), 8.70 (brd, 1H, NH). LR-MS-ES(±): Compatible with 368 MW.

Example 9

1-[4-[4-Amino-5-(3-fluorobenzoyl)thiazol-2-ylamino]piperidin-1-yl]ethanone (32468-252-1)

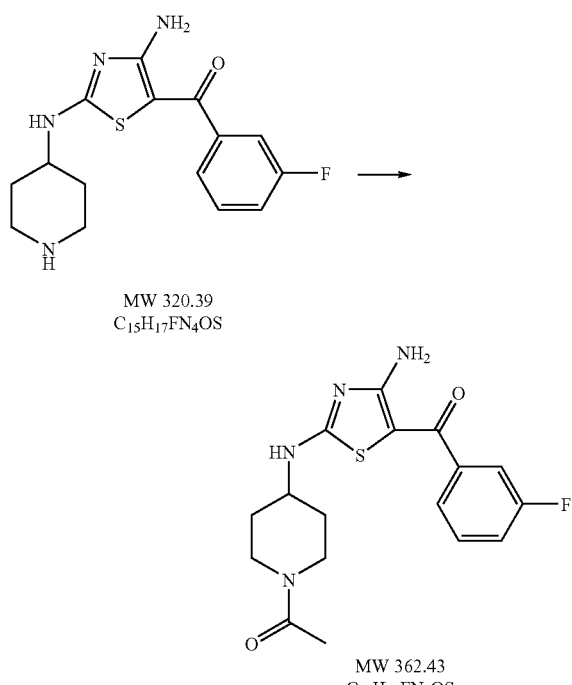

[4-Amino-2-(piperidin-4-ylamino)thiazol-5-yl]-(3-fluorophenyl)methanone (0.10 g, 0.31 mmol) (Example 6) was dissolved in a mixture of tetrahydrofuran (20 mL), chloroform (6 mL), and pyridine and cooled to −10° C. This was treated with acetyl chloride (0.032 g, 43 mmol) and stirred for 0.5 hr. at room temperature. This was diluted with cold methylene chloride (100 mL) and washed with 10% Na$_2$CO$_3$(aq) (2×). After drying (Na$_2$SO$_4$) and solvent removal, the residue was precipitated from a mixture of tetrahydrofuran and hexane to give 35 mg (30% yield) of 1-[4-[4-amino-5-(3-fluorobenzoyl)thiazol-2-ylamino]piperidin-1-yl]ethanone. $^1$H NMR (DMSO$_{-d6}$, 300 MHz) δ1.28 (m, 1H, CH), 1.41 (m, 1H, CH) 1.92 (m, 2H, CH$_2$), 2.75 (t, 1H, NCH), 3.14 (t, H, NCH), 3.32 (s, 3H, COCH$_3$), 3.6-4.0 (broad, 1H, CH), 3.77 (d, 1H, NCH), 4.22 (d, 1H, NCH), 7.31 (t, 1H, Aromatic), 7.38 (d, 1H, Aromatic), 7.48 (t, 1H, Aromatic), 7.51 (q, 1H, Aromatic), 8.01 (brd, 1H, NH), 8.48 (brd, 1H, NH), 8.72 (brd, 1H, NH). HRMS: (M+H)+: observed: 363.1288; calcd for 363.1286.

Example 10

[4-Amino-2-(1-methanesulfonylpipeidin-4-ylamino)thiazol-5-yl]-(3-fluoro-phenyl)methanone (32468-253-1)

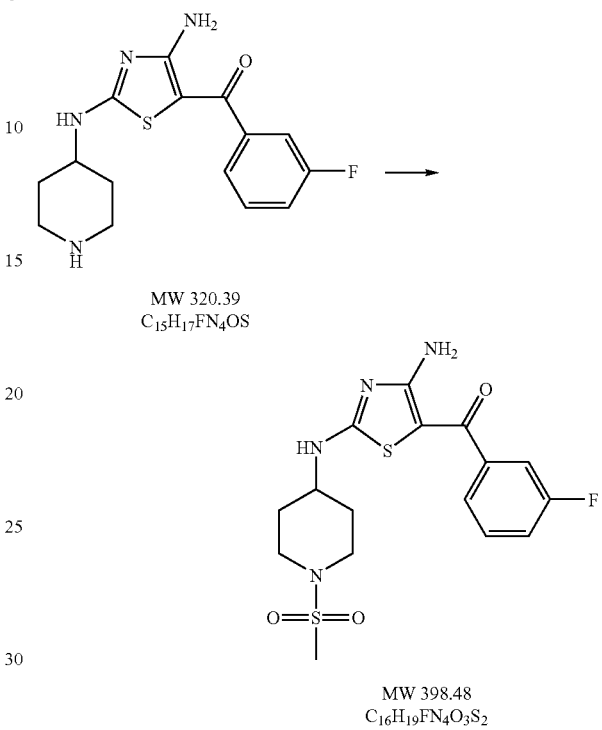

[4-Amino-2-(piperidin-4-ylamino)thiazol-5-yl]-(3-fluorophenyl)methanone (0.09 g, 0.28 mmol) (Example 6) was treated with methanesulfonyl chloride in a manner similar to Example 9 to give 35 mg (40% yield) of [4-amino-2-(1-methanesulfonylpipeidin-4-ylamino)thiazol-5-yl]-(3-fluorophenyl)methanone. $^1$H NMR (DMSO$_{-d6}$, 300 MHz) δ1.54 (m, 2H, CH$_2$), 2.03 (m, 2H, CH$_2$), 2.88 (m, 5H, NCH$_2$ & SCH$_3$), 3.6-4.0 (broad, 1H, CH),3.51 (d, 2H, NCH$_2$), 7.32 (t, 1H, Aromatic), 7.38 (d, 1H, Aromatic), 7.48 (t, 1H, Aromatic), 7.52 (q, 1H, Aromatic), 7.99 (brd, 1H, NH), 8.48 (brd, 1H, NH), 8.77 (brd, 1H, NH). HRMS: (M+H)+: observed: 399.0960; calcd for 399.0956.

Example 11

1-[4-[4-amino-5-(3-fluoro-4-methoxybenzoyl)thiazol-2-ylamino]piperidin-1-yl]ethanone (32468-250-1)

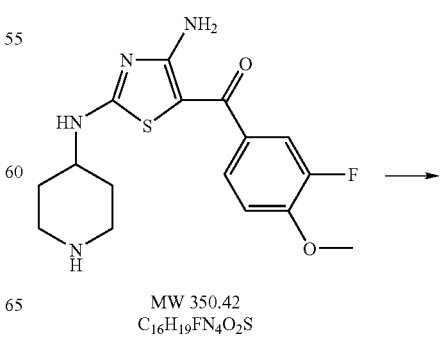

-continued

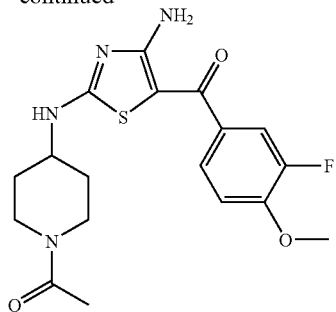

MW 392.45
C$_{18}$H$_{21}$FN$_4$O$_3$S

[4-Amino-2-(piperidin-4-ylamino)thiazol-5-yl]-(3-fluoro4-methoxy-phenyl)methanone (0.125 g, 0.36 mmol) (Example 7) was treated with acetylchloride in a manner similar to Example 9 to give 100 mg (77% yield) of 1-[4-[4-amino-5-(3-fluoro-4-methoxybenzoyl)thiazol-2-ylamino]piperidin-1-yl]ethanone. $^1$H NMR (DMSO$_{-d6}$, 300 MHz) δ1.38 (dm, 2H, CH$_2$), 1.92 (m, 2H, CH$_2$), 2.02 (s, 3H, COCH$_3$), 2.76 (t, 1H, NCH), 3.26 (t, 1H, NCH), 3.6-4.0 (broad, 1H, CH), 3.77 (m, 1H, NCH), 3.90 (s, 3H, OCH$_3$), 4.22 (m, 1H, NCH), 7.23 (t, 1H, Aromatic), 7.47 (t, 1H, Aromatic), 7.50 (t, 1H, Aromatic), 7.9-8.5 (brd, 2H, 2NH), 8.69 (brd, 1H, NH). HRMS: (M+H)+: observed: 393.1396; calcd for 393.1391.

Example 12

[4-Amino-2-(1-methanesulfonylpiperidin-4-ylamino)thiazol-5-yl]-(3-fluoro4-methoxy-phenyl)methanone (32468-255-1)

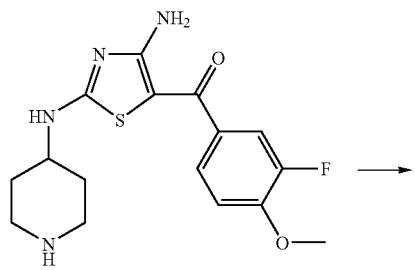

MW 350.42
C$_{16}$H$_{19}$FN$_4$O$_2$S

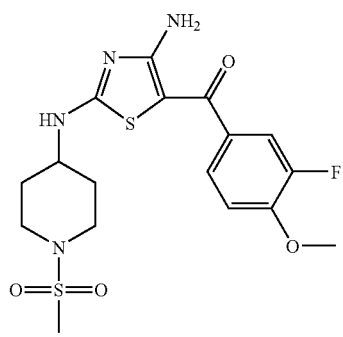

MW 428.51
C$_{17}$H$_{21}$FN$_4$O$_4$S$_2$

[4-Amino-2-(piperidin-4-ylamino)thiazol-5-yl]-(3-fluoro4-methoxy-phenyl)methanone (0.11 g, 0.31 mmol) (Example 7) was treated with methanesulfonyl chloride in a manner similar to Example 9 to give 30 mg (23% yield) of [4-amino-2-(1-methanesulfonylpiperidin-4-ylamino)thiazol-5-yl]-(3-fluoro-4-methoxy-phenyl)methanone. $^1$H NMR (DMSO$_{-d6}$, 300 MHz) δ1.46 (m, 2H, CH$_2$), 2.01 (m, 2H, CH$_2$), 2.90 (m, 5H, CH$_2$ & SCH$_3$), 3.55(m, 2HCH$_2$), 3.6-4.0 (broad, 1H, CH), 3.91 (s, 3H, OCH3), 7.24 (t,1H, Aromatic), 7.47 (t,1H, Aromatic), 7.59 (t,1H, Aromatic), 7.9-8.5 (brd, 2H, 2NH), 8.71 (brd, 1H, NH). HRMSEI: (M+H)+: observed: 428.0982; calcd for 428.0988.

Example 13

4-[4-Amino-5-(3-fluoro-4-methoxybenzoyl)thiazol-2-ylamino]piperidine-1-sulfonic acid dimethylamide (32468-258-1)

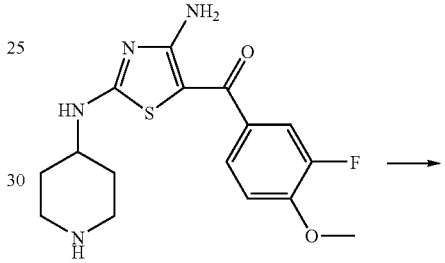

MW 350.42
C$_{16}$H$_{19}$FN$_4$O$_2$S

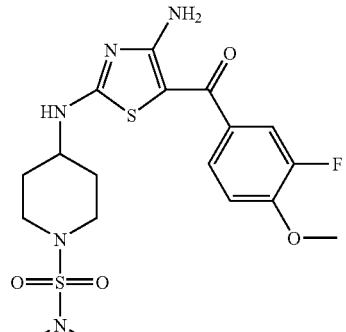

MW 457.55
C$_{18}$H$_{24}$FN$_5$O$_4$S$_2$

[4-Amino-2-(piperidin-4-ylamino)thiazol-5-yl]-(3-fluoro-4-methoxy-phenyl)methanone (0.08 g, 0.022 mmol) (Example 7)) was treated with dimethylsulfamoyl chloride in a manner similar to Example 9 except that diisopropylethylamine was additionally used as a catalyst and short plug of silica gel (ethyl acetate was used to pre-purify the sample to give 30 mg (22% yield) of 4-[4-amino-5-(3-fluoro-4-methoxybenzoyl)thiazol-2-ylamino]piperidine-1-sulfonic acid dimethylamide. $^1$H NMR (DMSO$_{-d6}$, 300 MHz) δ1.51 (m, 2H, CH$_2$), 1.97 (m, 2H, CH$_2$), 2.77 (s, 6H, 2× NCH$_2$), 2.99 (m, 2H, CH$_2$), 3.52 (m, 2H, CH$_2$), 3.6-4.0 (broad, 1H, CH), 3.89 (s, 3H, OCH$_3$), 7.9-8.5 (brd, 2H, 2NH), 8.71 (brd, 1H, NH). HRMS: (M+H)+: observed: 458.1331; calcd for 4581327.

Example 14

[4-Amino-2-(1-methanesulfonylpiperidin-4-ylamino) thiazol-5-yl]-(2,3-difluoro-6-methoxyphenyl)methanone (33245-290-A)

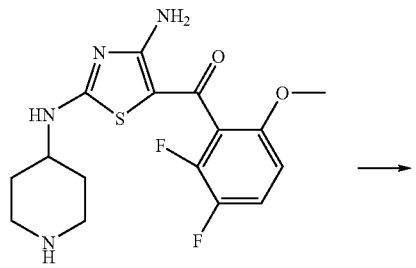

MW 368.41
$C_{16}H_{18}F_2N_4O_4S$

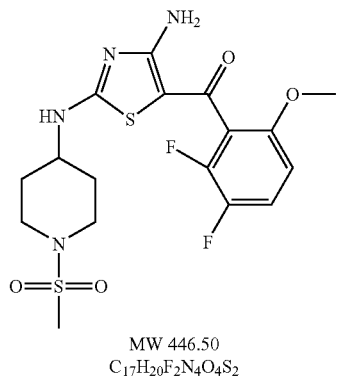

MW 446.50
$C_{17}H_{20}F_2N_4O_4S_2$

[4-Amino-2-(piperidin-4-ylamino)thiazol-5-yl]-(2,3-difluoro-6-methoxy-phenyl)methanone methanone (0.05 g, 0.14 mmol) (Example 8) was treated with methanesulfonyl chloride in a manner similar to Example 9 except that diisopropylethyl amine was additionally used as a catalyst to give 50 mg (90% yield) of [4-amino-2-(1-methanesulfonylpiperidin-4-ylamino)thiazol-5-yl]-(2,3-difluoro-6-methoxyphenyl)methanone. $^1$H NMR (DMSO$^{-d6}$, 300 MHz) δ1.57 (m, 2H, CH$_2$), 1.92 (m, 2H, CH$_2$), 2.85 (m, 5H, SCH$_3$ & NCH$_2$), 3.53 (m, 2H, NCH$_2$), 3.6-4.0 (broad,1H, CH), 3.88(s, 3H, OCH$_3$), 6.72 (m,1H, Aromatic), 7.42 (m,1H, Aromatic), 7.6 (2× brd, 1H, NH), 7.8 (brd, 1H, NH), 7.99 (m, 1H, Aromatic), 9.0 (brd, 1H, NH). LR/LC/MS: (M+H): compatible with 446. Ki CDK1=0.001 µM; Ki CDK2=0.001 µM; Ki CDK4=0.002 µM.

Example 15

Isothiocyanato-4-methanesulfonylbenzene (34960-186)

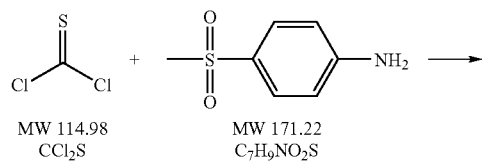

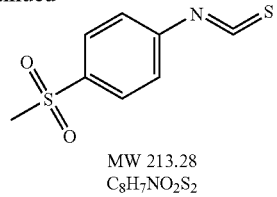

MW 213.28
$C_8H_7NO_2S_2$

A solution of 4-methanesulfonylphenylamine (2.4 g, 14 mmol) was dissolved in a mixture of water (30 mL) and hydrochloric acid (9 mL, 37%). This was treated drop wise at room temperature with thiophosgene (1.5 g, 13.2 mmol) with good stirring. After 1 h, the suspension was filtered, washed with water and dried over P$_2$O$_5$ to give 2.4 g (85% yield) of 1-isothiocyanato4-methanesulfonylbenzene. $^1$H NMR (CDCl3), 300 MHz δ3.09 (s, 3H, CH$_3$), 7.41(d, 2H, Aromatic), 7.98 (d, 2H, Aromatic).

Example 16

[4-Amino-2-(4-methanesulfonylphenylamino)thiazol-5-yl]-(2,3-difluoro-6-methoxyphenyl)methanone (34960-189-2)

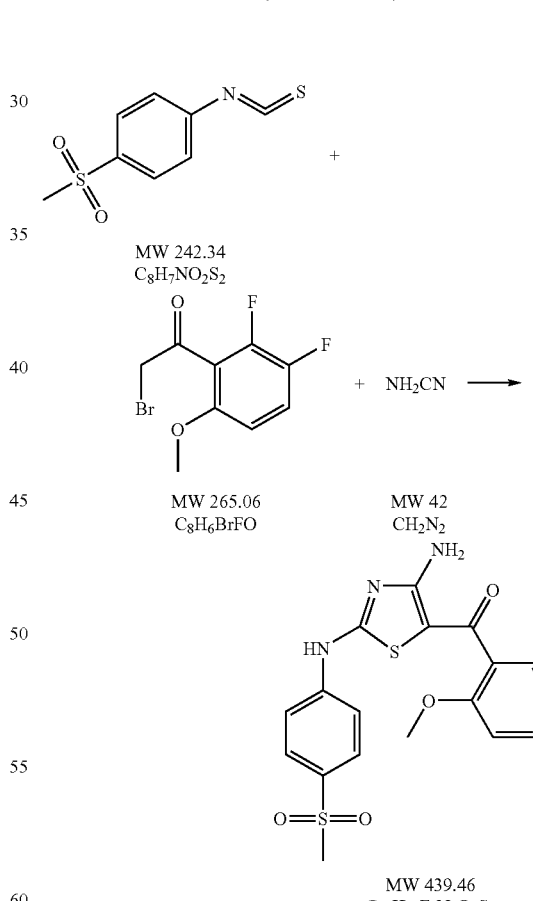

[4-Amino-2-(4-methanesulfonylphenylamino)thiazol-5-yl]-(2,3-difluoro-6-methoxyphenyl)methanone was prepared starting from the bromination of 1-(2,3-difluoro-6-methoxyphenyl)ethanone (Matrix) according to Example 2, followed by the diaminothiazole formation described in Example 3 to give a solid. This was purified by silica gel chromatography (2.5% methanol/methylene chloride) to give 15 mg (12% yield) of [4-amino-2-(4-methanesulfonylphenylamino)thiazol-5-yl]-(2,3-difluoro-6-methoxyphenyl)methanone after trituration of the pure fractions with ether and filtration. $^1$H NMR (DMSO$_{-d6}$, 300 MHz) δ3.18 (s, 3H, SCH$_3$), 3.68 (s, 3H, OCH$_3$), 6.95 (m, 1H, Aromatic), 7.50 (m,1H, Aromatic), 7.74 (dd, 4H, Aromatic), 8.2 (brd, 1H, NH), 11.21 (s, 1H, NH). HRMS: (M+H)+: observed: 440.0545; calcd for 440.0545.

Example 17

[4-Amino-2-(1-methanesulfonyl-piperidin-4-ylamino)thiazol-5-yl]-(2,6-difluorophenyl)methanone (34350-180-1PR)

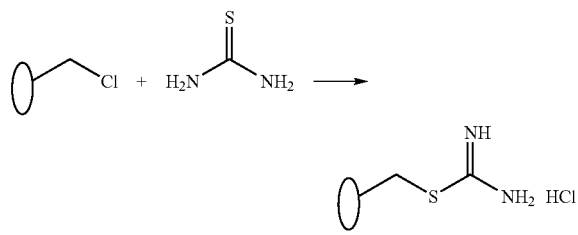

In a mixture of ethanol and 1,4-dioxane (500 mL, 1:4) was added Merrifield resin (50 g, with loading 4.3 mmol Cl/g, Fluka) and thiourea (5 eq, 82 g, 1.8 mol, Aldrich). The mixture was shaken at 85° C. for 5 days. After filtration, the resin was washed with dimethylformamide (3×50 mL), isopropanol (3×50 mL), dichloromethane (3×50 mL) and ethyl ether (3×50 mL). After drying the product resin in a desiccator for 3 days, 77.5 g of off white 2-methyl-isothiourea resin was obtained. Microanalysis indicated the product had a loading of 3 mmol/g.

4-[3-(2-methylisothioureido)thioureido-piperidine-1-carboxylic acid tert-butyl ester resin (34350-171)

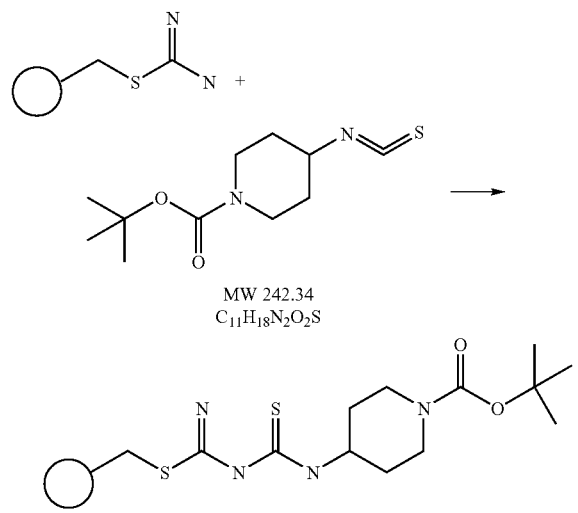

A 100 mL container was charged with methyl isothiourea resin (2.9 g) (Example 17a), a dimethylformamide solution of 4-isothiocyanatopiperidine-1-carboxylic acid tert-butyl ester (Example 1) and 4 equivalents of diisopropylethylamine. The mixture was shaken overnight at room temperature. The reaction mixture was filtered and the product resin was washed with dimethylformamide (3×30 mL), isopropyl alcohol (3×30 mL), dichloromethane (3×30 mL) and diethyl ether (3×30 mL) and then dried in a desiccator for three days. The off white product of 3.93 g was obtained with an analyzed loading of 1.8 mmol/g.

4-[4-Amino-5-(2,6-difluorobenzoyl)thiazol-2-ylamino-piperidine-1-carboxylic acid tert-butyl ester (34350-173-1)

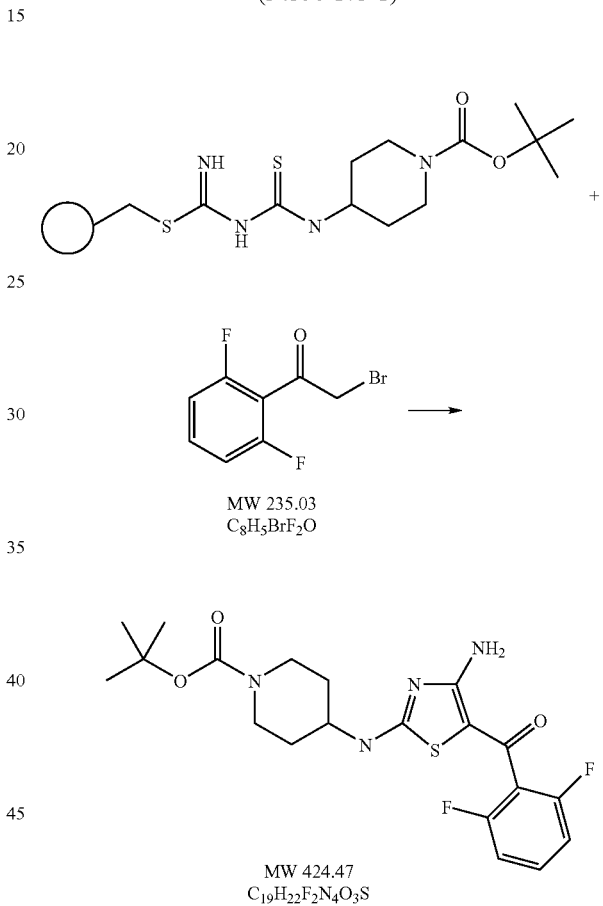

A flask was charged with a mixture of anhydrous dimethylformamide (10 mL), 4-[3-(2-methyl-isothioureido)thioureido]piperidine-1-carboxylic acid tert-butyl ester resin (0.60 g, 1.08 mmol), 2-bromo-1-(2,6-difluorophenyl)ethanone (0.616 g, 2.6 mmol, 2 eq) (Example 2), diisopropylethylamine, polymer bound (PS-DIEA, Aldrich) (823 mg, 3 eq) and was shaken overnight. Scavenger resin, PS-Trisamine (0.612 g, 2.5 eq, Argonaut) was added to the reaction mixture. The reaction mixture was shaken for overnight and then filtered through a short silica gel cartridge. The resin was washed with dichloromethane (3×10 mL) and the washing solution was combined with the original filtrate. The combined solution was concentrated and purified by silica gel chromatography. 0.276 g of 4-[4-amino-5-(2,6-difluorobenzoyl)thiazol-2-ylaminopiperidine-1-carboxylic acid tert-butyl ester was obtained as an off white solid (62% yield).

[4-Amino-2-(piperidin-4-ylamino)thiazol-5-yl]-(2,6-difluorophenyl)methanone (34350-179-1)

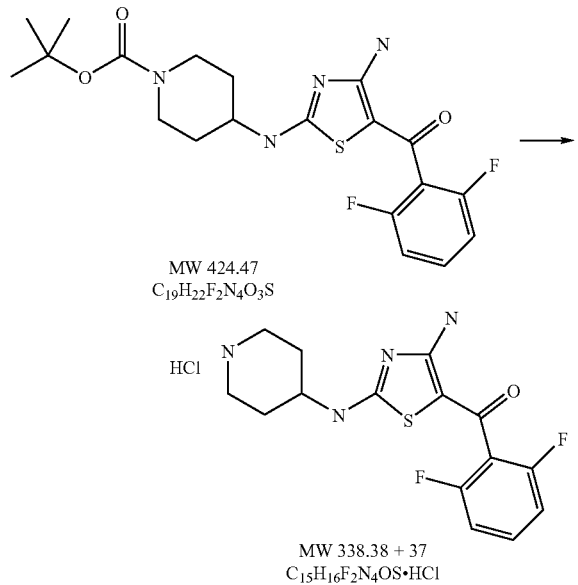

A flask containing 4-[4-amino-5-(2,6-difluorobenzoyl-thiazol-2-ylamino]piperidine-1-carboxylic acid tert-butyl ester (0.276 g, 0.63 mmol) was charged with of 4N HCl (2 mL) in 1,4-dioxane solution (10 mL). The mixture was stirred for 2 h at room temperature. The reaction mixture was concentrated and the residue was triturated with ethyl ether to afford 0.262 g of crude [4-amino-2-(piperidin-4-ylamino)thiazol-5-yl](2,6-difluorophenyl)methanone, which was used directly for next step.

[4-Amino-2-(1-methanesulfonylpiperidin-4-ylamino)thiazol-5-yl]-(2,6-difluorophenyl-methanone (34350-180-1)

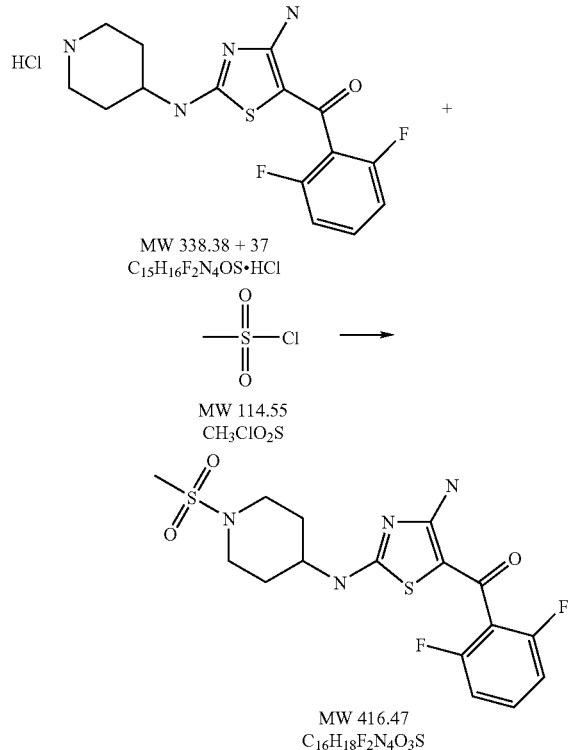

A flask was charged with [4-amino-2-(piperidin-4-ylamino)thiazol-5-yl]-(2,6-difluorophenyl)methanone (0.25 g, crude product from step D), anhydrous dichloromethane (1.5 mL) and methanesulfonyl chloride (3 eq, 155 uL). Then Diethylisopropyl amine (6 eq, 697 uL) was added to the above mixture. The reaction mixture was stirred at room temperature overnight. The reaction mixture was concentrated and the residue was purified through a silica gel column. 0.38 g of [4-amino-2-(1-methanesulfonylpiperidin-4-ylamino)thiazol-5-yl]-(2,6-difluorophenyl)methanone was obtained as a light brown solid. The overall yield for step D and E was 15%. $^1$H NMR (DMSO$_{-d6}$, 400 MHz): δ1.45-1.57 (m, 2H, CH$_2$), 1.95-2.05 (m, 2H, CH$_2$), 2.82-2.90 (m, 5H, CH$_3$, CH$_2$,), 3.45-3.55 (m, 2H, CH$_2$), 3.6-4.0 (broad, 1H, CH), 7.14-7.20 (m, 2H, Aromatic), 7.45-7.55 (m, 1H, Aromatic), 8.15-8.25 (broad, 1H, NH$_2$), 8.7-8.9 (broad, 1H, NH). HR-MS (M+H)$^+$: Observed: 417.0865: Calculated for 417.0861. Ki for CDK1 0.003 μM; CDK2 0.005 μM; CDK4 0.006 μM.

The pharmacological properties of the compounds of this invention may be confirmed by a number of pharmacological assays. The exemplified pharmacological assays which follow have been carried out with the compounds according to the invention and their salts. The compounds of the invention exhibited cdk4 activity with Ki values of less than 3 μM, preferably less than 0.5 μM; cdk2 activity with Ki values of less than 8 μM, preferably less than 0.5 μM, and cdk1 activity with Ki values of less than 10 μM, preferably less than 0.5 μM.

Example 18

Kinase Assays

Ki: Measurement

This experiment was conducted using recombinant human cyclin B-CDK1, human cyclin E-CDK2 or human cyclin D1-CDK4 complexes. GST-cyclinE (GST-cycE), CDK2, GST-cyclinB (GST-cycB), CDK1, GST-CDK4 and cyclin D1 (cycD1) cDNA clones in baculovirus vectors were provided by Dr. W. Harper at the Baylor College of Medicine, Houston, Tex. Proteins were co-expressed in High Five™ insect cells and the complex was purified on glutathione Sepharose resin (Pharmacia, Piscataway, N.J.) as previously described (Harper, J. W. et al. *Cell* 1993, 75, 805-816). A 6x-Histidine tagged truncated form of retinoblastoma (Rb) protein (amino acid 386-928) was used as the substrate for the cycD1-COK4, cycB-CDK1 and the cycE-CDK2 assays (the expression plasmid was provided by Dr. Veronica Sullivan, Department of Molecular Virology, Roche Research Centre, Welwyn Garden City, United Kingdom). The Rb protein is a natural substrate for phosphorylation by CDK4, CDK2 and CDK1 (see Herwig and Strauss *Eur. J. Biochem. Vol.* 246 (1997) pp. 581-601 and the references cited therein).

The expression of the 62 Kd protein was under the control of an IPTG inducible promoter in an M15 *E. coli* strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialysed against 20 mM HEPES pH 7.5, 30% glycerol, 200 mM NaCl, and 1 mM DTT. Purified Rb fusion protein stocks were quantitated for protein concentration, aliquoted, and stored at −70° C.

Using the protein constructs described above, CDK1, CDK2, and CDK4 HTRF assays were set up. These were done in 96-well format and read in 384-well plate format. The assays were run at 3× their respective Kms for ATP.

In the CDK4 assay, test compounds were diluted to 3× ntheir final concentrations in 25 mM Hepes, pH 7.0, 6.25 mM $MgCl_2$, 1.5 mM DTT, 135 μM ATP. The DMSO concentration was no greater than 4.76%. Twenty microliters were added to the wells of a 96-well plate. The kinase reaction was initiated by the addition of 40 μl/well of a solution containing 0.185 μM Rb and 2.25 μ/ml CDK4 in 25 mM Hepes, pH 7.0, 6.25 mM $MgCl_2$, 0.003% Tween-20, 0.3 mg/ml BSA, 1.5 mM DTT. Blank wells without CDK4 were included. The plates were incubated at 37° C. for 30 minutes with shaking. The kinase reaction was terminated by the addition of 15 μl/well of 1.6 uM anti-phospho-Rb (Ser 780) antibody (Cell Signaling Inc.) in 25 mM Hepes, pH 7.0, 24 mM EDTA, 0.2 mg/ml BSA. After 30 minutes at 37° C., 15 μl/well of 3 nM Lance-Eu-W1024 labeled anti-rabbit IgG and 60 nM Allophycocyanin conjugated anti-His 6 (PerkinElmer Life Sciences) in 25 mM Hepes, pH 7.0, 0.5 mg/ml BSA were added. Following a one hour incubation at 37° C., 35 μl of each well, in duplicate, were transferred to 384-well black plates. The plates were read using either ViewLux or Victor V readers (PerkinElmer Life Sciences) using an excitation wavelength of 340 nm and dual emission wavelengths of 615 nm and 665 nm. IC50 values (the concentration of test compounds reducing the assay control fluorescence read-out by 50%) were first calculated from net readings at 665 nm, normalized for europium readings at 615 nm. For ATP competitive inhibitors, the Ki values were calculated according to the following equation:

$Ki = IC50/(1+S/Km)$ where S refers to the substrate concentration (ATP) and Km refers to the Michaelis-Menten constant for the ATP.

The CDK1 and CDK2 assays were similarly run except for small differences in reagent and protein concentrations:

The compound and enzyme buffers for both assays contained 10 mM $MgCl_2$.

For CDK1 and CDK2, the respective reagent ATP concentrations were 162 uM and 90 uM. CDK1 at a reagent concentration of 0.15 ng/ul and CDK2 at a reagent concentration of 0.06 ng/ul were used. Reagent concentrations of detection reagents were adjusted between 3-12 nM Eu-Ab and 60-90 nM APC-antiHis 6 to give signal to background ratios of at least 10 to 1.

Example 19

Tablet Formulation

| Item | Ingredients | Mg/Tablet | | | | | |
|---|---|---|---|---|---|---|---|
| 1 | Compound A * | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

* Compound A represents a compound of the invention.

Manufacturing Procedure

Mix Items 1, 2 and 3 in a suitable mixer for 15 minutes.
Granulate the powder mix from Step 1 with 20% Povidone K30 Solution (Item 4).
Dry the granulation from Step 2 at 50° C.
Pass the granulation from Step 3 through a suitable milling equipment.
Add the Item 5 to the milled granulation Step 4 and mix for 3 minutes.
Compress the granulation from Step 5 on a suitable press.

Example 20

Capsule Formulation

| Item | Ingredients | mg/Capsule | | | | |
|---|---|---|---|---|---|---|
| 1 | Compound A * | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

Compound A represents a compound of the invention.

Compound A represents a compound of the invention.

Manufacturing Procedure

Mix Items 1, 2 and 3 in a suitable mixer for 15 minutes.
Add Items 4 & 5 and mix for 3 minutes.
Fill into a suitable capsule.

Example 21

Injection Solution/Emulsion Preparation

| Item | Ingredient | mg/mL |
|---|---|---|
| 1 | Compound A * | 1 mg |
| 2 | PEG 400 | 10-50 mg |
| 3 | Lecithin | 20-50 mg |
| 4 | Soy Oil | 1-5 mg |
| 5 | Glycerol | 8-12 mg |
| 6 | Water q.s. | 1 mL |

Compound A represents a compound of the invention.

Manufacturing Procedure

Dissolve item 1 in item 2.
Add items 3, 4 and 5 to item 6 and mix until dispersed, then Homogenize.
Add the solution from step 1 to the mixture from step 2 and Homogenize until the dispersion is translucent.
Sterile filter through a 0.2 μm filter and fill into vials.

Example 22

Injection Solution/Emulsion Preparation

| Item | Ingredient | mg/mL |
|---|---|---|
| 1 | Compound A * | 1 mg |
| 2 | Glycofurol | 10-50 mg |
| 3 | Lecithin | 20-50 mg |
| 4 | Soy Oil | 1-5 mg |
| 5 | Glycerol | 8-12 mg |
| 6 | Water | q.s. 1 mL |

Compound A represents a compound of the invention.

Manufacturing Procedure

Dissolve item 1 in item 2.

Add items 3, 4 and 5 to item 6 and mix until dispersed, then homogenize.

Add the solution from step 1 to the mixture from step 2 and homogenize until the dispersion is translucent.

Sterile filter through a 0.2 μm filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

The invention claimed is:

1. A compound of the formula

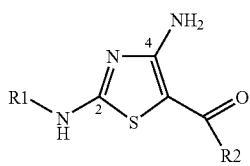

I wherein
$R^1$ is

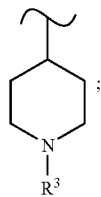

;

$R^2$ is phenyl which may be substituted by up to four substituents independently selected from halogen or $OR^5$;
$R^3$ is selected from the group
H,
$CO_2R^6$,
$C(O)R^6$;
$SO_2R^6$, and
$SO_2NR^5R^6$;
$R^5$ and $R^6$ are each independently selected from the group consisting of:
H and lower alkyl
or the pharmaceutically acceptable salts or esters thereof.

2. The compound of claim 1 wherein the phenyl is substituted by fluorine.

3. The compound of claim 2 wherein the fluorine is on the 3-position of the phenyl ring, said ring being further optionally substituted by fluoro or methoxy.

4. The compound of claim 2 wherein the phenyl is substituted by $OR^5$.

5. The compound of claim 4 wherein the $R^5$ is lower alkyl.

6. The compound of claim 1 selected from the group consisting of:
4-[4-Amino-5-(3-fluorobenzoyl)thiazol-2-ylamino]piperidine-1-carboxylic acid tert-butyl ester
4-[4-Amino-5-(3-fluoro4-methoxybenzoyl)thiazol-2-ylamino]piperidine-1-carboxylic acid tert-butyl ester
4-[4-Amino-5-(2,3-difluoro-6-methoxybenzoyl)thiazol-2-ylamino]piperidine-1-carboxylic acid tert-butyl ester,
[4-Amino-2-(piperidin-4-ylamino)thiazol-5-yl]-(3-fluorophenyl)methanone,
[4-Amino-2-(piperidin-4-ylamino)thiazol-5-yl]-(3-fluoro-4-methoxyphenyl)methanone,
[4-Amino-2-(piperidin-4-ylamino)thiazol-5-yl]-(2,3-difluoro-6-methoxyphenyl)methanone, and
1-[4-[4-Amino-5-(3-fluorobenzoyl)thiazol-2-ylamino]piperidin-1-yl]ethanone.

7. The compound of claim 1 selected from the group consisting of:
[4-Amino-2-(1-methanesulfonylpipeidin-4-ylamino)thiazol-5-yl]-(3-fluoro-phenyl)methanone,
1-[4-[4-amino-5-(3-fluoro-4-methoxybenzoyl)thiazol-2-ylamino]piperidin-1-yl]ethanone,
[4-Amino-2-(1-methanesulfonylpiperidin-4-ylamino)thiazol-5-yl]-(3-fluoro-4-methoxy-phenyl)methanone,
4-[4-Amino-5-(3-fluoro-4-methoxybenzoyl)thiazol-2-ylamino]piperidine-1-sulfonic acid dimethylamide,
[4-Amino-2-(1-methanesulfonylpiperidin-4-ylamino)thiazol-5-yl]-(2,3-difluoro-6-methoxyphenyl)methanone, and
[4-Amino-2-(1-methanesulfonyl-piperidin-4-ylamino)thiazol-5-yl]-(2,6-difluorophenyl)methanone.

8. The compound of claim 1 which is [4-Amino-2-(4-methanesulfonylphenylamino)thiazol-5-yl]-(2,3-difluoro-6-methoxyphenyl)methanone.

9. A pharmaceutical composition comprising as an active ingredient an effective amount of a compound of claim 1 and a pharmaceutically acceptable carrier or excipient.

10. The pharmaceutical composition of claim 1 which is suitable for parenteral administration.

11. A method for treating a breast or colon tumor comprising administering to a subject in need of such treatment a therapeutically effective amount of at least one compound according to claim 1.

* * * * *